US012044676B2

(12) United States Patent
Souza

(10) Patent No.: US 12,044,676 B2
(45) Date of Patent: *Jul. 23, 2024

(54) 3D CELL VIABILITY ASSAY

(71) Applicant: Greiner Bio-One North America, Inc., Monroe, NC (US)

(72) Inventor: Glauco R. Souza, Houston, TX (US)

(73) Assignee: GREINER BIO-ONE NORTH AMERICA, INC., Monroe, NC (US)

( * ) Notice: Subject to any disclaimer, the term of this patent is extended or adjusted under 35 U.S.C. 154(b) by 1268 days.

This patent is subject to a terminal disclaimer.

(21) Appl. No.: 16/379,730

(22) Filed: Apr. 9, 2019

(65) Prior Publication Data
US 2019/0242881 A1    Aug. 8, 2019

Related U.S. Application Data

(63) Continuation of application No. 13/995,610, filed as application No. PCT/US2012/021233 on Jan. 13, 2012, now Pat. No. 10,288,603.

(60) Provisional application No. 61/438,310, filed on Feb. 1, 2011.

(51) Int. Cl.
| | |
|---|---|
| *G01N 33/50* | (2006.01) |
| *B03C 1/00* | (2006.01) |
| *B82Y 25/00* | (2011.01) |
| *C12N 11/00* | (2006.01) |
| *C12N 13/00* | (2006.01) |
| *C12Q 1/02* | (2006.01) |
| *C12N 5/07* | (2010.01) |
| *G01R 33/12* | (2006.01) |
| *H01F 1/06* | (2006.01) |
| *H01F 1/08* | (2006.01) |
| *H01F 1/113* | (2006.01) |
| *H01F 1/44* | (2006.01) |

(52) U.S. Cl.
CPC .......... *G01N 33/5088* (2013.01); *B03C 1/00* (2013.01); *B82Y 25/00* (2013.01); *C12N 11/00* (2013.01); *C12N 13/00* (2013.01); *C12Q 1/02* (2013.01); *G01N 33/5082* (2013.01); *C12N 5/06* (2013.01); *G01N 2333/435* (2013.01); *G01R 33/1269* (2013.01); *H01F 1/063* (2013.01); *H01F 1/083* (2013.01); *H01F 1/113* (2013.01); *H01F 1/445* (2013.01)

(58) Field of Classification Search
CPC .......... G01N 33/5088; G01N 2333/00; G01N 2333/435; C12N 13/00; C12N 5/06; C12N 2333/435; C12N 1/00; C12N 1/12; B03C 1/00; B03C 1/02; B82Y 25/00; H01F 1/00; H01F 1/44; H01F 1/445; C11B 1/025; C11B 1/04; C12R 1/89; C12P 5/007

See application file for complete search history.

(56) References Cited

U.S. PATENT DOCUMENTS

2006/0134076 A1    6/2006 Bitar

OTHER PUBLICATIONS

Fukuda et al., Biomaterials, 27:1061-1070, 2006. (Year: 2006).*

(Continued)

*Primary Examiner* — Allison M Fox
*Assistant Examiner* — Qing Xu
(74) *Attorney, Agent, or Firm* — Boulware & Valoir PLLC

(57) ABSTRACT

Cells are grown in 3D culture and topological features obtained by photomicrography are correlated to cell viability and cell interactions.

18 Claims, 13 Drawing Sheets

(56) References Cited

OTHER PUBLICATIONS

Kim et al., Japanese Journal of Applied Physics, 47:1325-1328, 2008 (Year: 2008).*
Rabbani et al., IFMBE Proceedings, 25:219-221, 2009 (Year: 2009).*
Mendes et al., Physica A, 298:471-487, 2001 (Year: 2001).*
Souza et al., Nature Nanotechnology, 5:291-296, published on Mar. 14, 2010 (Year: 2010).*
Hubert Tseng et al., Abstract 177: A Novel Vascular "Ring" Assay for Smooth Muscle Contractility Using Magnetic 3-Dimensional Bioprinting, American Heart Association's Arteriosclerosis, Thrombosis and Vascular Biology 2014 Scientific Sessions, May 2014—vol. 34, Issue suppl_1, Poster Abstract #177 (2014).
Bernard Ho, et al., Integrin-Linked Kinase in the Vascular Smooth Muscle Cell Response to Injury, American Journal of Pathology, 173, No. 1, pp. 278-288 (Jul. 2008).
Guillaume Morissette, et al., Inhibition of human and rabbit arterial smooth muscle cell migration mediated by the kinin B1 receptor: role of receptor density and released mediators, Can. J. Physiol. Pharmacol., 84: 1107-1119 (2006).

\* cited by examiner

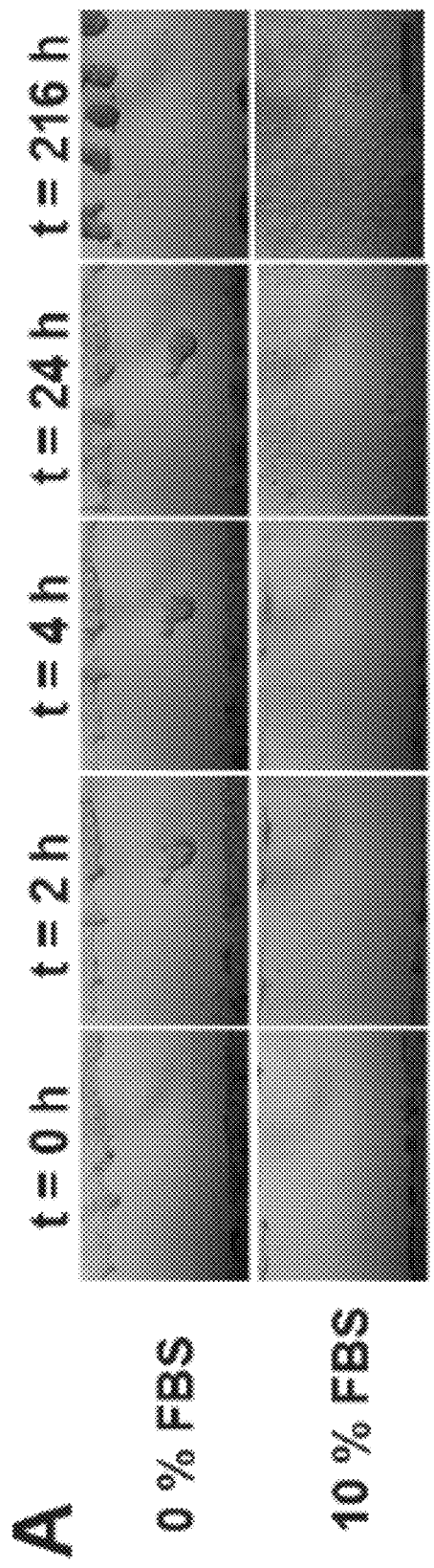
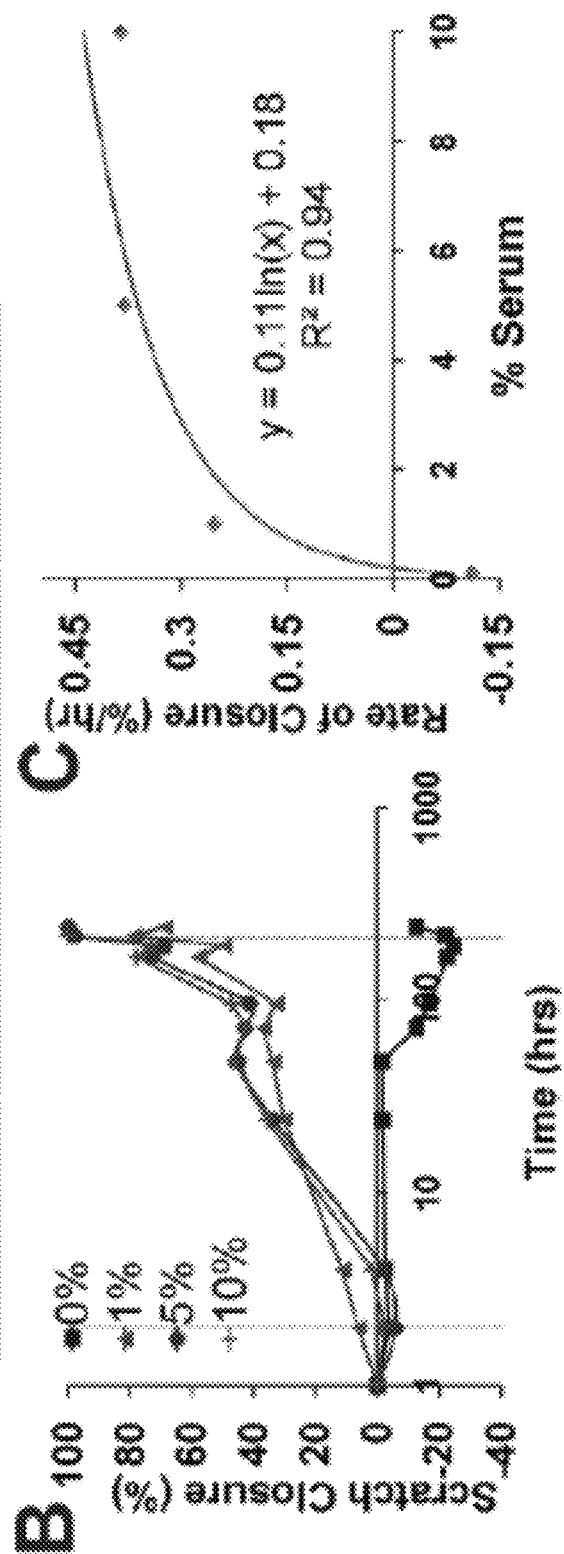
FIGURE 11

3D CELL VIABILITY ASSAY

PRIOR RELATED APPLICATIONS

This application is a continuation of U.S. patent application Ser. No. 13/995,610, filed 19 Jun. 2013, which is a 35 USC 371 national phase filing of International Application No. PCT/US2012/021233, filed 13 Jan. 2012, which claims priority to U.S. Provisional Application No. 61/438,310, filed 1 Feb. 2011, all of which are incorporated by reference herein in their entirety.

FEDERALLY SPONSORED RESEARCH STATEMENT

Not applicable.

REFERENCE TO MICROFICHE APPENDIX

Not applicable.

FIELD OF THE INVENTION

The invention relates to the fields of cell assays for diagnostics, toxicology, drug discovery, as well as image analysis, nanotechnology, materials, medicine, cellular biology, and tissue engineering. More particularly, the compositions and methods of the present disclosure relate to methods of magnetizing cells, 3D cell culturing, cell levitation, cell manipulation, and cell patterning using magnetic fields, as well as image analysis methods and label-free, real-time detection with applications in toxicity testing, drug testing, high-throughput screening, high-content screening, cell viability, cell-cell interaction, wound healing and cell culture optimization assays.

BACKGROUND OF THE INVENTION

Most drug recalls and delays in regulatory approvals result from drug-induced adverse events, and the most frequent reasons for withdrawal of an drug are nephrotoxicity and hepatotoxicity. For example, two widely prescribed non-steroidal anti-inflammatory drugs (NSAIDs), ibuprofen and acetaminophen, are known nephrotoxic[1] and hepatotoxic compounds, respectively. However, the mechanisms of NSAID toxicity and the events that produce cell death are poorly understood and our methods of assessing these side effects before use in patients are of limited usefulness.

Current in vitro 2D cell-based assays are easy and inexpensive to perform, as well as amenable to automation and scale up. Unfortunately, 2D systems are often poor predictors of drug-induced hepatotoxicity and can yield false-positives because 2D cultured cells tend to be more sensitive to cytotoxic agents.

Furthermore, the 2D environment does not reflect a natural cellular environment and is not able to model extracellular stresses, such as oxidative and osmotic stress. As an example, kidney cells cultured in 2D in vivo, as compared to those from cell culture models, are likely to be more susceptible to nephrotoxins because of hyperosmolality, but this is difficult (if not impossible) to model in 2D cell cultures. Therefore, 3D tissue models, which can capture cell-cell and cell-matrix interactions and provide a more in vivo-like environment and offer a better platform for toxicity testing.

Materials are being developed that can support three-dimensional (3D) cell culturing conditions. Most of the work in 3D cell culture techniques to date involves rotation of the flasks, the use of an exterior scaffold to which the cells can adhere, the use of magnetic fields to suspend cells, or some combination of these approaches.

For example, Felder in US2005054101, WO2005010162 describes a hydrogel substrate that forms an exterior scaffolding in which cells can grow and be supported in a 3D environment. This introduces an artificial substrate with which cells interact, rather than rapidly promoting cell-cell interactions, and although an improvement over 2D culturing, the scaffolding is likely to perturb the cells and remains in the finished product. Further, cells can grow on or in the microcarriers, but cells cannot be levitated in a manner where all around cell-cell contact and interaction is possible.

There is also a significant level of complexity involved in the fabrication of the microcarriers of Felder, which includes laborious chemistry and the need for complex equipment. Further, algimatrix, one of the main reagents in making the microcarriers, can be a source of endotoxins. Buoyancy control also seems to be relevant to facilitate levitation, and is controlled by the infusion of glass bubbles into the microcarriers, again contributing to complexity and difficulty. Finally, specialized hardware is required for agitation, which is needed achieve gas exchange and to prevent clumping of the microcarriers, and impellers are often used to agitate cells. However, the shear stress resulting from agitation is known to cause cell damage. Furthermore, agitation impairs any magnetic shape control of 3D cultures.

Becker in US2009137018, WO2005003332 uses a coating of bioattractive magnetized core particles, thereby initiating adherence of the biological cells to the magnetized core particles and allowing their suspension in a magnetic field. The coating remains with the cells during culture, thus introducing an unnatural element in the culture and probably perturbing the cells. The inventors contemplate the use of a biodegradable coating that could eventually be eliminated, but none are disclosed, so it is not known if this approach would be successful. Furthermore, because cells are grown on the core of the microcarriers, the levitation of individual cells so they can be brought together by magnetic levitation for the purpose of promoting cell-cell interaction is unlikely to take place. Therefore, it is not obvious that the rapid (hours) assembly of 3D multicellular structures due to cell-cell contact can be demonstrated when using microcarriers. Also, by growing cells on the microcarriers, the co-culture of different cells types, especially by levitating individual cells and then bringing them together magnetically, is not demonstrated. Finally, this system is cumbersome and not suitable for scale-up and high-throughput applications.

A better approach might be to temporarily magnetize cells, allowing for their 3D culture. For example, Akira in US2006063252, WO2004083412, WO2004083416 uses magnetic cationic liposomes (MCL) to magnetize cells by uptake of the liposomes. The magnetized cells are then grown in a sheet on the bottom of a plate using magnetic attraction, and then released for use. However, although able to produce sheets of cells, the cells are still grown on the bottom of a plate, and thus this is not true 3D culturing by magnetic levitation. Further, no functional assay was demonstrated.

Shimizu and Akira et al. recently used magnetic guidance to seed cells onto a decellularized blood vessel. Their study shows encouraging results, but they do not use the magnetized cells as the source of tissue to be decellularized. The magnetized cells are only used to recellularize the decellularized blood vessels.

In patent application WO2010036957 by Souza, cells are levitated in a magnetic field by contacting the cells with a "hydrogel" comprising a bacteriophage with nanoparticles that are responsive to a magnetic field. In particular, filamentous phage, such as fd, f1, or M13 bacteriophage, are used. How the method works is not completely clear, but it is theorized that the phage provide a gel-like structure or assembly that coats the cells, and somehow assists the cells to uptake or adsorb the magnetically responsive nanoparticles. Thus, even when the hydrogel is washed away, the cells remains magnetically responsive, and can be levitated in an appropriate magnetic field. However, although the hydrogel is mostly washed away, the potential for phage infectivity or transfer of genetic material remains, and thus it is desired to provide a material that allows cell uptake or adsorption without the use of phage.

WO2011038370, also by Souza, describes a second generation hydrogel, which completely avoids the use of bacteriophage to enable the magnetization of cells. Furthermore, a variation of the claimed gels is now commercially available at N3D BIOSCIENCES™, under the trade name NANOSHUTTLE.™ This new hydrogel provides a superior method of magnetizing cells without the use of any toxic or infectious agents, and the cells remain magnetized when the gel is washed away.

Although some of these approaches are promising, there is still room for improved 3D methods of assessing drug toxicity that more accurately model a natural environment, and that are robust, reproducible and amenable to scale up.

SUMMARY OF THE INVENTION

| Abbreviation | Definition |
|---|---|
| $D_f$ | Fractal dimension, a statistical quantity that gives an indication of how completely a fractal appears to fill space and is used herein to approximate the number of cells in multicellular 3D structures generated by MLM, determined by equation 3, below. |
| ECM | Extracellular matrix |
| FBS | Fetal Bovine Serum |
| Kg | a constant called the structure prefactor, which is often empirically determined and can vary depending on the system being measured and the type of measurement$^2$. Here, it was arbitrarily chosen as 0.8 since the modeled system mirrors the experimental data. |
| MLM | magnetic levitation method |
| MTT | 3-(4,5-dimethylthiazol-2-yl)-2,5-diphenyl tetrazolium bromide], used in a prior art cell viability or proliferation assays based on enzymatic conversion of the substrate MTT to a purple color. |
| HPF | human primary fibroblast |
| SMC | smooth muscle cells |
| HEK | Human Embryonic Kidney |
| BrEpic | Bronchial Epithelial |
| NIR | Near-infrared spectroscopy |

The present invention provides an improved label-free, real-time cell viability assay. The method uses 3D cell culturing by magnetic levitation and couples the 3D culture technique with image analysis to assess cell viability and cell-cell interaction.

By "culturing" herein, we include culturing single cell types or co-culturing more than one cell type.

Generally speaking, the cell viability detection method is based on the principal that dead cells will lyse, thus either lose any magnetically responsive particles and therefore no longer levitate, or the death of cells will cause 3D cell clusters to disintegrate. Thus, only live cells will be imaged in the method. Increasing cell death will result in more, but smaller and more diffuse or porous cell clusters. Furthermore, because fractal dimension is a function of both structure and number of cells N, the replication of viable cells will increase N, consequently increase the fractal dimension of the multicellular structures.

The invention also allows us to monitor and measure cell viability (cell health) or cell-cell interactions in response to any test agent (including cells and extracellular matrix proteins as agents) introduced into culture or an environmental change. The technique is novel in that we combine rapid formation of 3D cell culture by magnetic levitation with image analysis of topological parameters for quantifying cell viability or cell-cell interactions. The method can be simply described, as follows:

1. First the cells are levitated to allow 3D culture growth.
2. Low magnification (4×) photomicrographs are taken of the 3D cells.
3. Those photomicrographs are analyzed using e.g., imageJ software (freeware) to measure e.g., fractal dimension, the number of cell clusters, cell cluster size, tissue opening, and/or total area of cell clusters, and other cell parameters as described throughout. This step can be done at any time during or after the experiment.
4. Next, a drug candidate or an agent (including but not limited to drugs, environmental toxins, growth factors, inhibitors, nanoparticles, homogeneous or heterogeneous mixture of cells, and/or homogeneous or heterogeneous mixture of extracellular matrix proteins and/or peptides) is added to the cells, usually in a dose and/or time dependent configuration (e.g, different samples have differing doses of drug).
5. Steps 2 and 3 are repeated.
6. Finally, the output of the image analysis (e.g., including but not limited to, fractal dimension, number of cell clusters, area size of clusters, total area of clusters) is plotted as a function of time and/or drug concentration and that data is used to determine the effect of the test agent on the cells.

Test agents can be anything whose toxicity is desired to be assayed, including drugs, other cell types, cell components, suspected toxins or any environmental or industrial agent or chemical.

Although described in a linear, stepwise fashion above, this is only for ease of understanding, and usually all samples (zero drug control, plus multiple samples with increasing doses of drug) can be processed in parallel. In the alternative, samples can be grown for 1-7, preferably 2-3 days, to attain a sufficient size, and drug added at a later time point.

Furthermore, although we have used a simple ring magnet herein, it is known how to influence 3D culture shape and structure by varying the magnetic field. Finally, although it is preferred to use magnetic levitation, as described herein, any 3D culturing method can be used in the method.

Preferably, the photo's are taken while the cells are still levitating because this is expected to minimize disruption to the culture. However, this is not essential, and a 3D culture can be photographed when not levitating. This may be particularly appropriate for some assays, such as wound healing assays wherein one measures the rate of closure of a gap or hole in a multicell structure.

Preferably, the control sample image (no drug or agent) is assigned to be a 100% viability reference value, and the lowest dosage that produces total cell death is assigned to be the 0% viability reference value. Thus, any values in between should reflect the toxicity of the drug or agent. These calculations are similar to those used for various colorimetric agents, such as MTT, the difference being that other methods use color and the inventive method uses topological variables, such as fractal dimension, and therefore, avoids the addition of any signal reporting chemical or labeling agent.

As a test of the system, we compared MTT data from 2D cultures with our 3D method (FIG. 3) and found the results to be comparable, although the 3D structure provides a protective effect to cells on the interior of the culture, reflected in a significant increase in cell viability.

In more detail, the invention is a cell viability assay comprising culturing levitated cells to form 3D cell structures, taking photomicrographs of said cells at one or more times (it is not required that cells be levitated during photography, but it is preferred to minimize disruptions to the culture), analyzing said photomicrographs to measure one or more of i) fractal dimension, ii) the number of cell clusters, iii) cell cluster size, iv) cell culture texture, v) total area of cell clusters, and/or vi) rate of wound closure or tissue opening (herein referred as wound closure). Finally, fractal dimension, rate of wound closure, and cell cluster size are directly proportional to cell viability or cell-cell interactions, and the number of cell clusters and total area of cell clusters are inversely proportional to same.

There can also be a plurality of samples of levitated cells, said samples being with and without one or more concentrations of various test agents or having test agents added at one or more times. Generally, a decrease in cell viability with said test agent indicates that the test agent is inhibitory, and wherein an increase in cell viability indicates that said test agent is stimulatory. The same method can assess a large number of variables, including agent toxicity, growth stimulation, mitotic stimulation, wound healing, cell-cell interactions, cell size, cell sprouting, cell structural changes, and the like.

Further, although we have focused on viability and cell-cell interactions herein, the method can also provide important information about cell shape and structure, which correlates with important changes in cell status. For example, some cells become rounder on transformation to a cancerous cell, endothelial cells sprout/elongation during angiogenesis process, and the like.

Further, the method can be combined with other methods, e.g., cell and nuclear staining, and effects on cell size, nuclear/cytoplasmic ratio, cell roundness, and the like can also provide important information about cell status. These assays can either be performed after test agent effects on cell viability and/or cell differentiation (in the case of stem cells) have been ascertained by photomicrography, or separate samples can be prepared for same.

In some embodiments, the invention is a cell viability or cell-cell interaction assay comprising: culturing a 3D cell culture with one or more cell types; taking photomicrographs of said 3D cell culture at one or more times; analyzing said photomicrographs to measure one or more of i) fractal dimension, ii) the number of cell clusters, iii) cell cluster size, iv) cell culture texture, or v) total area of cell clusters, wherein fractal dimension and cell cluster size are directly proportional to cell viability, cell-cell interactions, cell migration, extracellular matrix formation, cell-extracellular matrix interaction, or type and/or number of cells present in the culture, and the number of cell clusters and total area of cell clusters are inversely proportional to cell viability, cell-cell interactions, or cell types present in the culture. Rate of wound closure also correlated directly with cell-cell interactions, cell migration, extracellular matrix formation, cell-extracellular matrix interaction, and viability.

The method can include culturing a plurality of 3D cultures for use as control cultures and a culturing a plurality of 3D cultures for use as test cultures, wherein a test agent is added to said test cultures and assessing the effect of said test agent on said cell viability, cell-cell interactions, cell-extracellular matrix interaction, or cell types present in the culture (when co-culturing cells).

The method can also include adding varying amounts of said test agent to said a plurality of test cultures, taking a plurality of photomicrographs of said 3D cell culture at a plurality of times, and/or washing out said test agent and taking a further plurality of photomicrographs of said 3D cell culture at a further plurality of times.

In preferred embodiments, the cells are levitated with a composition comprising: a) a negatively charged nanoparticle; b) a positively charged nanoparticle; and c) a support molecule, wherein one of said negatively charged nanoparticle or positively charged nanoparticle contains a magnetically responsive material, such as iron or iron oxide, and wherein said support molecule holds said negatively charged nanoparticle and said positively charged nanoparticle in an intimate admixture.

Preferably, the support molecule comprises peptides, polysaccharides, nucleic acids, polymers, poly-lysine, fibronectin, collagen, laminin, BSA, hyaluronan, glycosaminoglycan, anionic, non-sulfated glycosaminoglycan, gelatin, nucleic acid, extracellular matrix protein mixtures, antibody, or mixtures or derivatives thereof, b) wherein said negatively charged nanoparticle is a gold nanoparticle, and c) wherein said positively charged nanoparticle is an iron oxide nanoparticle. Most preferred, the composition is NANOSHUTTLE™.

In some embodiments $D_f=[\log(N)-\log(kg)]/\log(L/a)$ and $D_f$ is the fractal dimension, kg is the structure prefactor and is a constant, N is the number of cells, a is the diameter of a cell, and L is length of the box. Further, $$\text{Cell viability} = \frac{D_{f sample} - D_{f 100\% \text{ cell death}}}{D_{f control} - D_{f 100\% \text{ cell death}}},$$

and $D_{f\,sample}$ is the fractal dimension of the test culture, and $D_{f control}$ is the fractal dimension of the control. However, other methods can be used for calculating same.

In wound closure assays, there are two approaches for generating a wound: one, the 3D culture is perforated to form a wound, and the other 3D culture is mechanically shredded and then magnetically patterned into a ring structure. In both cases, a test agent can be added to said wounded 3D culture, and $$\text{Wound closure } (\%) = 100\% - \left(\frac{\text{area of wound}_t}{\text{area of wound}_{t0}} \times 100\right),$$

wherein area of wound$_t$ is the area of the wound at a given time after addition of a test agent, and the area of wound$_{t0}$ is the area of the wound before said test agent is added.

The cell assay can be used in a variety of applications, including at least to assess the effects of a test agent on toxicity, wound healing, mitotic activity, growth stimulation, cell-cell interactions, viability, or cell structure, and the like.

$$D_f = [\log(N) - \log(kg)] / \log(L/a)$$

where 1 unit (a) is the diameter of a cell and the length (L) of the box was 9.8 units. Kg is a constant called the structure prefactor, which is arbitrarily chosen to be 0.8 herein. The number of cells (N) varies. The calculated fractal dimension ($D_f$) values are (a) 1.47, (b) 1.59, (c) 1.86, and (d) 1.94 for the four structures. Thus, the $D_f$ is proportional to cell viability.

Figure 5:
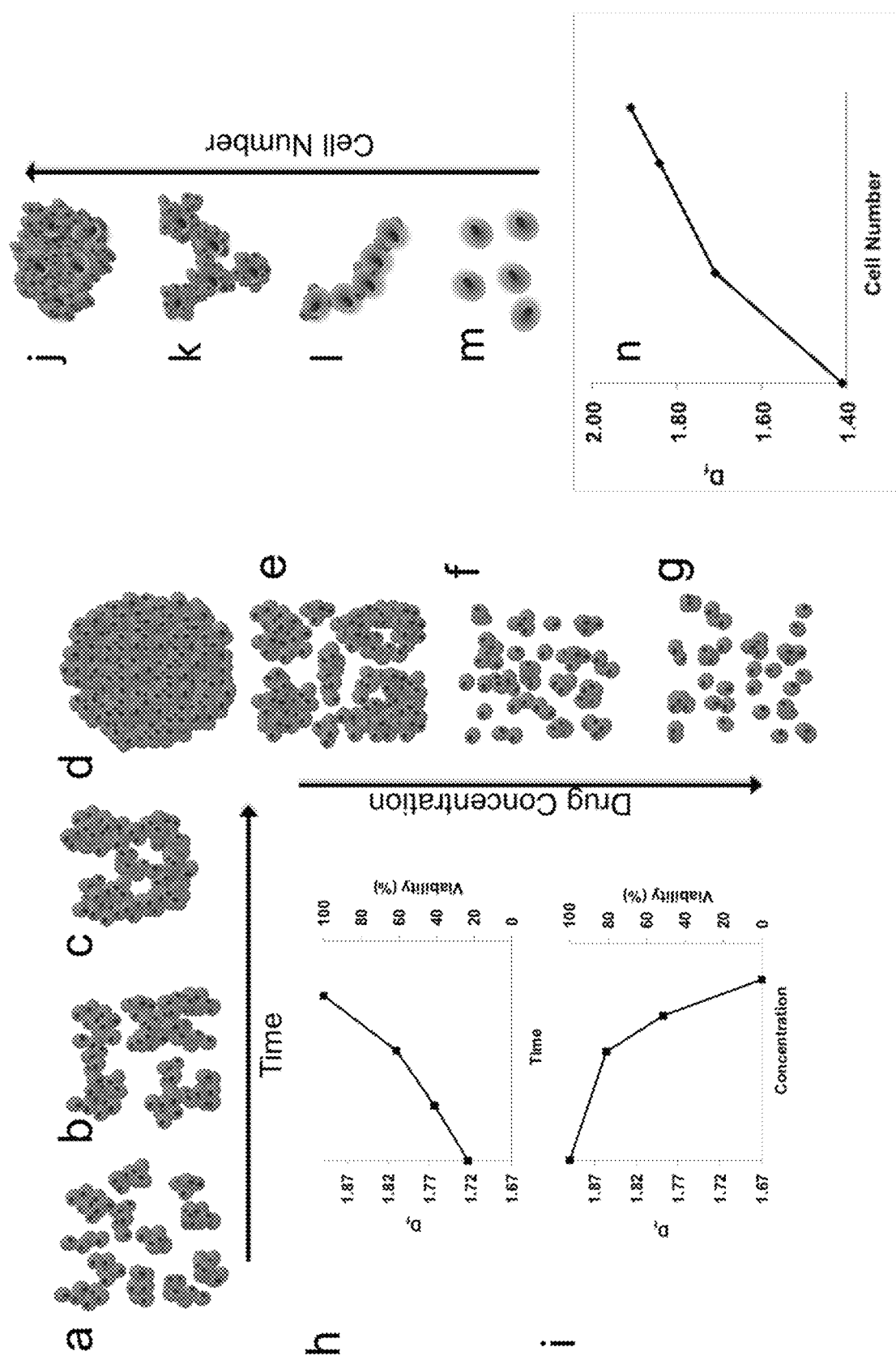

FIG. 5. Simulated 3D cell culture growth with one (a-g) or two (j-m) cell types over time. Parts a-g represent a healthy culture growing over time, wherein increasing drug is added to cultures d-g. Parts h-i represent plots of cultures d-g exposed to increasing drug dosage concentrations or time. The calculated $D_f$ values are (a) 1.7265, (b) 1.7678, (c) 1.8144, (d) 1.8935, (e) 1.7195, (f) 1.6734, and (g) 1.5405. $D_f$ and viability versus healthy culture growth over time (h) and drug/toxin concentration (i). Parts j-m represent a healthy co-culture of two cell types where there is an increasing number of one cell type (small ovals). Part n represents plot of cultures j-m with increasing number of cells of one cell type (small ovals) where the other cell type (large ovals) is kept constant. The calculated $D_f$ values are (j) 1.418, (k) 1.812, (l) 1.844, and (m) 1.912. $D_f$ versus cell number of one cell type of a co-cultured simulated system (n).

Figure 6:
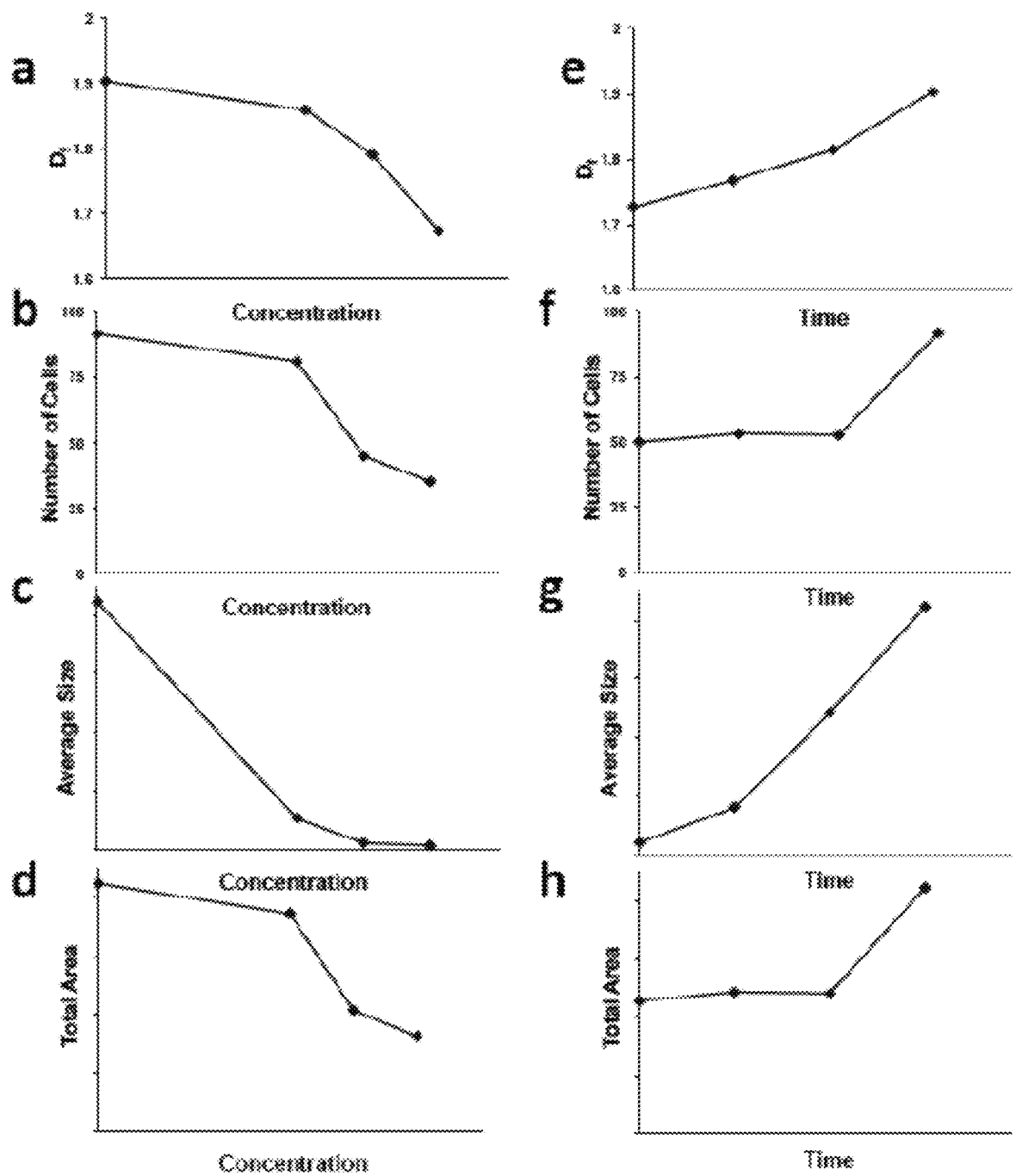

FIG. 6. Various plots based on simulated data. (a) $D_f$ versus concentration, (b) number of cells versus concentration, (c) average size versus concentration, (d) total area versus concentration, (e) $D_f$ versus time, (f) number of cells versus time, (g) average size versus time, and (h) total area versus time.

Figure 7:
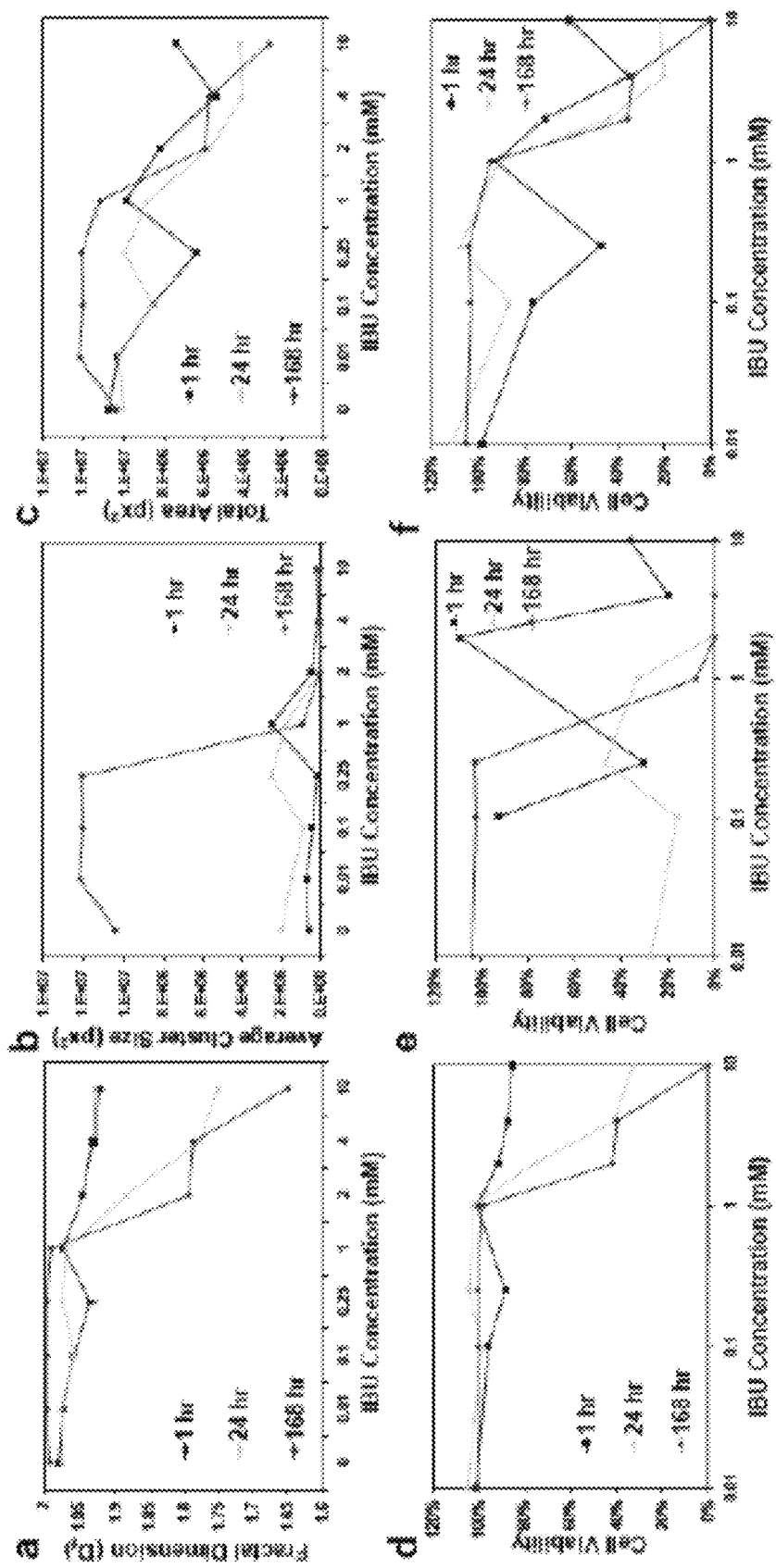

FIG. 7. Various plots based on physical data shown in FIG. 2. (a) Fractal Dimension ($D_f$), (b) Average Cluster Size (px$^2$), and (c) Total Area (px$^2$) for HEK293 cells exposed to varying concentrations of ibuprofen for 1, 24, and 168 hours. Cell viability based on (d) Fractal Dimension ($D_f$), (e) Average Cluster Size, and (f) Total Area (where px$^2$ is an arbitrary unit of area and stands for pixel squared). The 0 mM concentration contains DMSO, but no drug.

Figure 8:
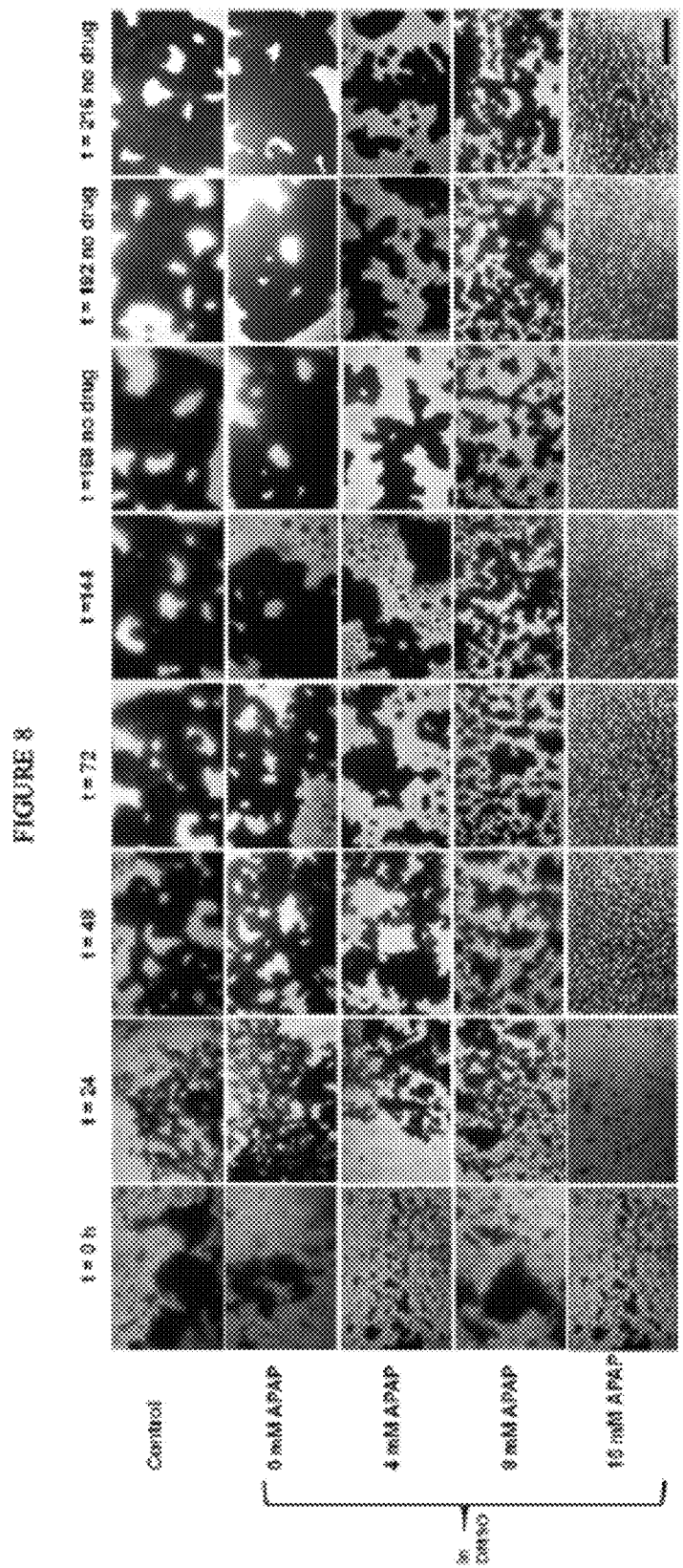

FIG. 8. Phase contrast micrographs show 3D hepatocyte morphology at 4× magnification under untreated conditions (control) and after treatment with 4 and 8 mM acetaminophen ("APAP") for 0, 24, 48, 72, 144 hours, followed by recovery without APAP at 168, 192, and 216 hours after the initial drug dosage (scale bar is 500 μm).

Figure 9:
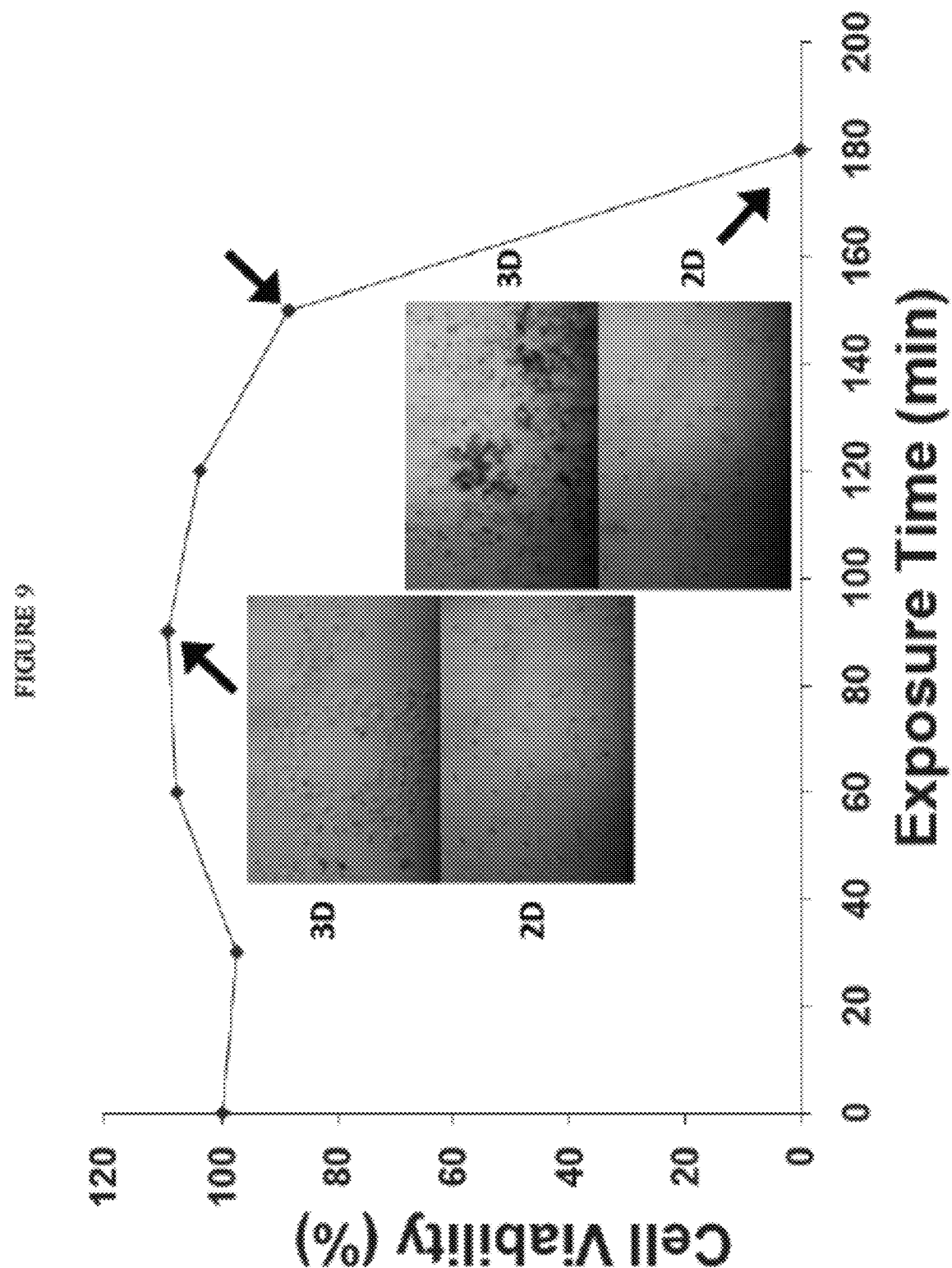

FIG. 9. Bronchial Epithelial ("BrEpic") cell viability versus exposure time to xylene. The cells in 3D die (top right panel, right arrow points to plotted 0% viability), or completely lose their squamous or tile like structure characteristic of healthy epithelia (top left panel, first arrow points to plotted 100% viability) after the final exposure to xylene (3D) (middle arrow points to last exposure time point). This is important for toxicity testing of airborne factors, where we can levitate the tissue to the air-liquid interface and expose the cells to a gas. To show that only the cells at the air liquid interface were affected, we also show the cells that we co-cultured in 2D at the bottom of the xylene exposed petri-dish (right and left bottom panel).

Figure 10:
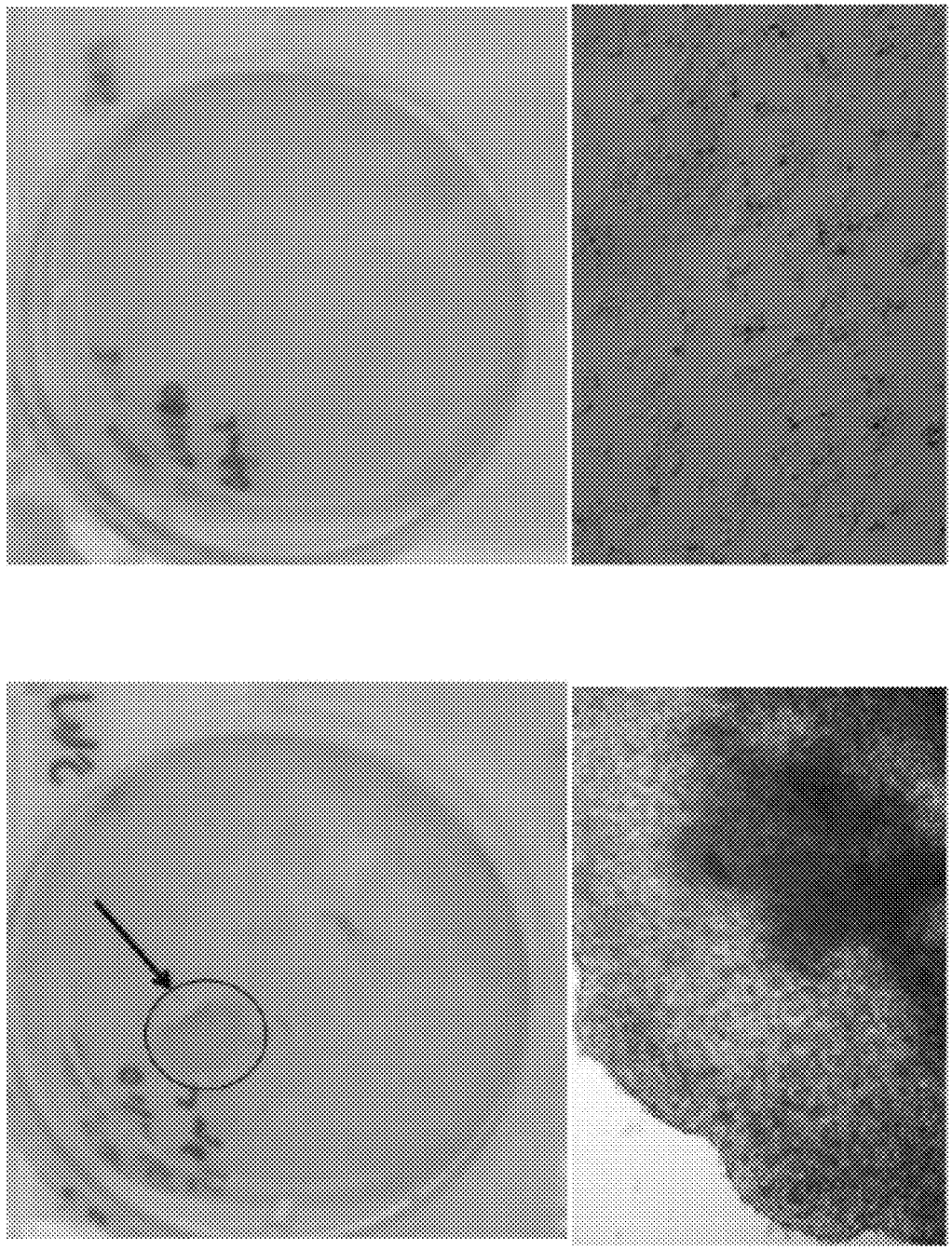

FIG. 10. Photographs of HEK293 tissue sheets grown in non-adherent and adherent cell culture dishes.

FIG. 11. (A) Microphotographs of HEK293 cells grown in 2D showing scratch closure as a function of time (0, 2, 4, 24 and 216 hours) with media supplemented with 0 or 10% FBS (4× magnification, scale bar is 500 μm). (B) Percent of scratch closure as a function of time for media supplemented with 0, 1, 5 and 10% FBS. The rate of closure is found by fitting the data between the dashed lines. (C) Rate of closure versus % serum using the data shown in (C).

Figure 12:
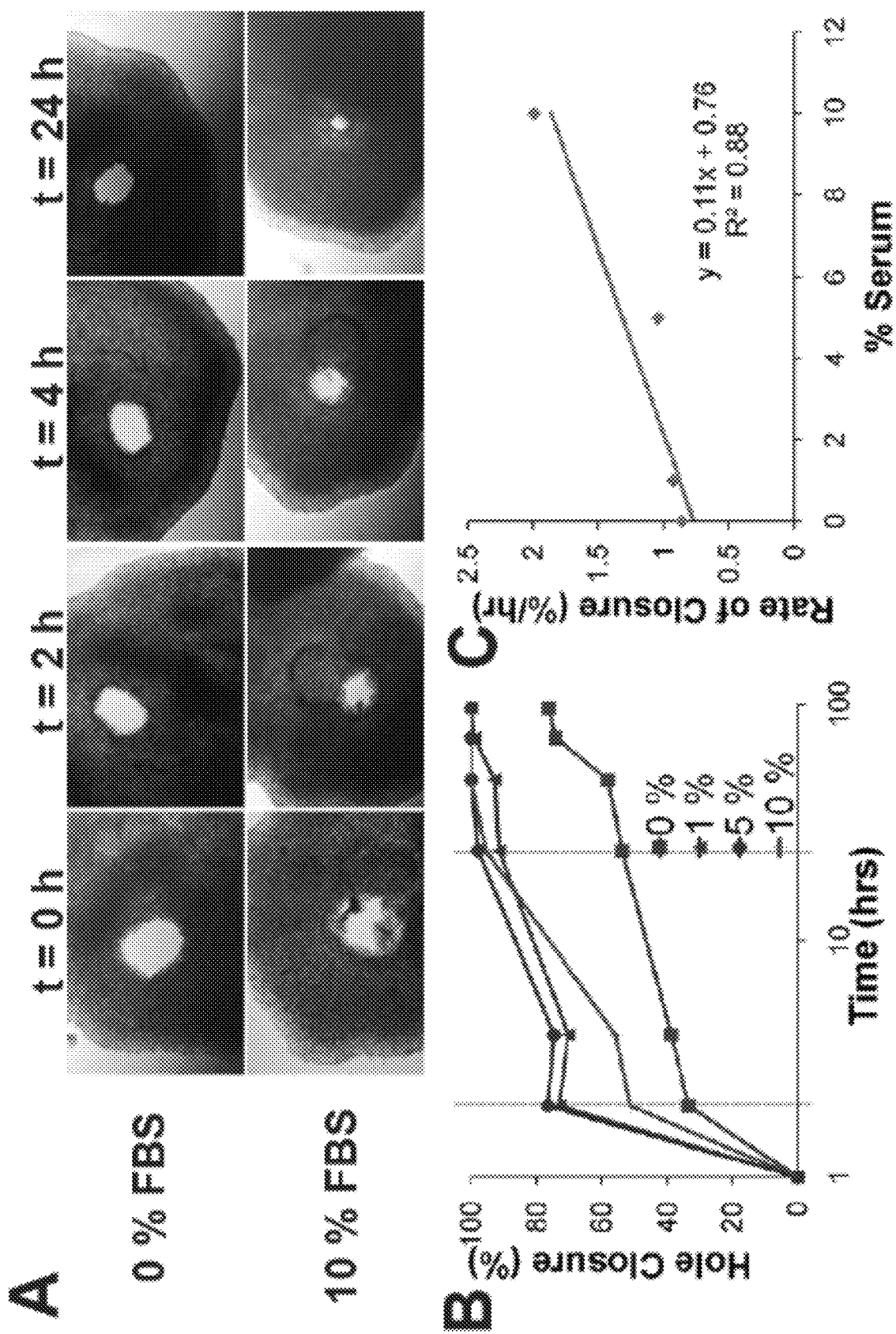

FIG. 12. (A) Microphotographs of HEK293 cells grown in 3D showing hole closure as a function of time (0, 2, 4, and 24 hours) with media supplemented with 0% or 10% FBS (4× magnification, scale bar is 500 μm). (B) Percent of hole closure as a function of time for media supplemented with 0, 1, 5 and 10% FBS. The rate of closure is found by fitting the data between the dashed lines. (C) Rate of closure versus % serum using the data shown in (B).

Figure 13:
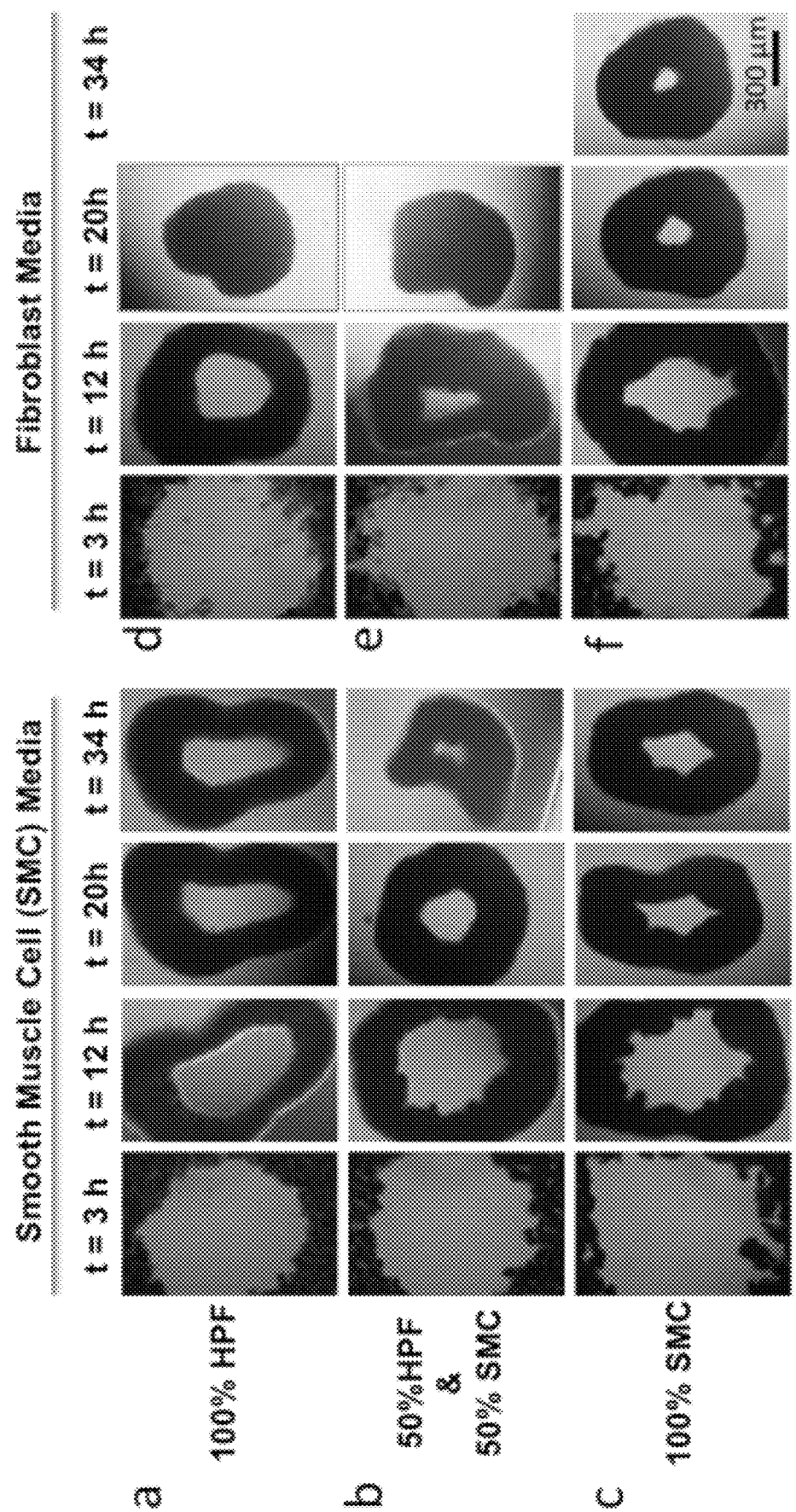

FIG. 13. Microphotographs of human primary fibroblast (a and d; HPF; 500,000 cells) and smooth muscle cells (c and f; SMC; 500,000 cells) cultures and co-culture (1:1; HPF-SMC) of human primary fibroblast (250,000 cells) with smooth muscle (250,000 cells) cells (b and e) grown in 3D showing hole closure as a function of time (3, 12, 20, and 34 hours) when cultured in smooth muscle (a-c, left) or fibroblast (d-f, right) media (SCIENCELL RESEARCH LABORATORIES,™ Carlsbad, CA; Fibroblast Medium, Catalog Number: #2301; and Smooth Muscle Cell medium, Catalog Number: #1101 media; 2.5× magnification, scale bar is 300 μm).

DESCRIPTION OF EMBODIMENTS OF THE INVENTION

The present invention is a label-free detection method that evaluates and quantifies cell viability or cell-cell interactions by combining 3D cell culturing by magnetic levitation and/or magnetic guidance, and image analysis of topological features, including fractal dimension analysis. The cohesiveness of the structure of 3D cell cultures is sensitive to presence of toxicants or other agents, regardless of whether their mode of action impair cells viability, growth or cell-cell interactions. Therefore we apply fractal dimension analysis and other topological tools to quantify cell viability resulting from changes in 3D multicellular structure changes in term of for example, fractal dimension, 3D culture size, wound size, and number of cell clusters etc. as a function of toxicant concentration and/or time.

Clear advantages of the inventive include: 1. label-free assessment of viability, 2. the ability to monitor viability as a function of time without disturbing or destroying the sample, 3. only a standard inverted microscope (transmitted light, equipped with camera) and cell culture equipment is required, 4. the use of 3D culture is a great improvement over the use 2D monolayers, 5. the technique is adaptable to high-throughput, and 6. the amount of information gathered can be increased by collecting images at different planes (thus providing more 3D data) using confocal or deconvolution microscopy, real time imaging, spectral resolved imaging (such as hyperspectral imaging) and/or fluorescence microscopy.

Another advantage of this technique is that it is not sensitive to the size of multicellular structures as long as the field chosen for fractal dimension analysis is filled. Fractal dimension is sensitive to both cell-cell interactions, which brings cells together, and cell viability and growth, as shown below.

In fractal geometry, the fractal dimension, D, is a statistical quantity that gives an indication of how completely a fractal appears to fill space, as one zooms down to finer and finer scales. There are many specific definitions of fractal dimension. The most important theoretical fractal dimensions are the Rényi dimension, the Hausdorff dimension and packing dimension. The box-counting dimension and correlation dimension are widely used, partly due to their ease of implementation. Herein we have employed the box-counting methodology, but it is possible to use other methods provided the method is consistently employed.

This analysis technique allows one to obtain data as a function of drug dosage time without the need for extra samples for each time point, which are required for current fluorescent and colorimetric assays. The magnetic levitation method or "MLM" coupled with fractal dimensional analysis appears to be a valuable tool for in vitro toxicological studies on kidney cells, hepatocytes, and lung cells, and many other cell types, and even mixtures of cell types that form tissue like structures.

Further, drugs can be washed out and recovery assessed. Thus each 3D cell culture can function as its own control, and this further improves the reliability of the results.

Additional improvements can be made by coupling this technique to measurement of transmitted light intensity, cell auto-fluorescence detection, fluorescence detection, 3D deconvolution or confocal microscopy, darkfield (or scattered light) microscopy, and/or multiphoton microscopy.

Chemiluminescence could also be coupled to this system, but the addition of a chemiluminescent substrate might compromise viability and compromise the value of a label-free technique. The same is true with fluorescence, since modified cells (such as GFP expressing cells) or fluorescent molecules would be needed to be introduced to culture, therefore, possibly compromising the viability of the system and making it no longer label-free. However, NIR detection/imaging could also be used and there may be instances where the advantages outweigh the disadvantages of adding an artificial label to the system.

Furthermore, the $D_f$ values and $D_f$ changes as a function of time are expected to be characteristic of each cell type, cell lineage, and cell composition within the same culture. Therefore, this invention could be used to tabulate the $D_f$ of various cell types and co-culture of cells, with the purpose of using this method to identify and differentiate different cell types or mixture of cells.

This invention could also be used to evaluate protein interactions resulting from cell-cell interactions. Because 3D cell culture formation is often mediated by the interaction between cell membrane proteins during cell-cell contact, the number and distribution of these proteins at the cell membrane and the dissociation constant of these proteins should also influence $D_f$. For example, 3D cultures from cells with larger number of these surface proteins distributed evenly around the cell, should show higher $D_f$ (tighter clusters) than systems with lower protein cell coverage and/or with proteins localized (or focused) at specific cell positions. This also suggests that cell polarization could also influence $D_f$. Such analysis could also be used when studying the inhibition of cell-surface proteins or when silencing genes responsible for the production of such a protein (such as when using sRNA, but not limited to it). Blocking proteins at the cell surface, by using antibodies or peptides for example, could also influence changes in $D_f$. Therefore, changes in levels of protein expression and protein accessibility should influence changes in $D_f$. The method will thus allow measurement of various cell-cell interactions and testing of agents that disrupt same.

Finally, this type of image analysis could also be used with 3D cultures that are not magnetically levitated, where these cultures grow on a surface, in a matrix, and/or clustered in 3D at the bottom of a well or on another surface. However, there are drawbacks for other culture methods relative to using our magnetic levitation method. The clear advantage of magnetic levitation method is its capability to bring cells together rapidly and keep them together while monitoring $D_f$ and other topological variables. When using other cell culturing systems, cells can be dispersed over large areas making it difficult to sample and analyze images. Besides, all the disadvantages associated with other culturing systems also apply to evaluating viability, and 3D cultures more closely approximate natural tissues.

Example 1: Materials & Methods

Cell lines and cell culture: Human Embryonic Kidney (HEK293) cells were purchased from American Type Cell Culture (ATCC™, Cat. No. CRL-1573). HEK293 were propagated using a base medium of Dulbecco's Modified Eagle Medium (DMEM) (MEDIATECH™ INC., 10-017-CV) supplemented with fetal bovine serum (ZEN-BIO™, SER-500), Pen-Strep (SIGMA-ALDRICH™, P4333), HEPES (99%, for biochemistry, ACROS ORGANICS, 1725-71000), and Sodium Bicarbonate (SIGMA-ALDRICH™, S-8875). Phosphate Buffered Saline (PBS) (SIGMA-ALDRICH™, P4417-100TAB) and Trypsin/EDTA 1× (MEDIATECH™ INC., 25-053-C1) were used to subculture the cells. All cultures were incubated at 37° C. under a 5% $CO_2$ atmosphere. Cells were centrifuged for 1.5 minutes at ~1380 RCF.

Compounds:

(+/−)-Ibuprofen (SIGMA ALDRICH™, 1110) was dissolved in Dimethyl Sulfoxide (DMSO) (FISHER SCIENTIFIC™, BP2311). Positive controls consisted of treating cells with the same stock solution used for delivering compounds without any toxin added at a concentration of 1% in the medium. Negative controls consisted of cells without treatment of the stock solution.

Imaging of the wound area was performed using a LEITZ™ Labovert FS inverted microscope. Image analysis on the bright field microscopy images was performed with IMAGEJ 1.43u software. In the ImageJ program, the image file was opened and the scale was set to a unit length in mm. With the image maximized, the area of the scratch or hole was traced using the paintbrush tool and a black line was drawn around the edge of the linear scratch or hole. The area of the scratch or hole was determined by first selecting the wand tool, then selecting the painted black line, and finally selecting measure. The resulting area was then recorded.

2D Scratch Assay:

HEK293 cells were cultured to >90% confluence in adherent culture dishes and scratches were created by manually scraping a 200 μL pipette tip (with an approx. diameter of 0.90 mm) along the cell monolayer. The 6-well cell culture plates used for 2D culture were sterile, non-treated multidishes for suspension cell cultures (NUNC™, 150239). Markings were made on the outside of the culture dish as reference points for image acquisition so that the same area could be monitored over time.

3D Wound Assay:

Levitated 3D cell cultures were generated using the 6-well Bio-Assembler™ kit (NANO3D BIOSCIENCES™, INC.) consisting of NANOSHUTTLE™ solution, a 6-well plate magnetic drive, and a 6-well tissue culture plate. The NANOSHUTTLE™ solution is a nanoparticle assembly solution of iron oxide nanoparticles ($Fe_2O_3$) and Au nanoparticles assembled in an aqueous solution of poly-L-lysine which promotes the cellular uptake of nanoparticles.

The magnetic drive is an acrylic mount carrying 6 cup magnets from APPLIED MAGNETS™ (Plano, TX, Model Number: Cup-32) or 24 cylinder magnets from K&J MAGNETS™ (Jamison, PA, Model Number: D48-N52). The field value at the center of the meniscus where the cells reside when levitated, approximately at 18 mm (6-well system) and 4 mm (24-well system) below the magnet bottom, is 300 G. The fields were calculated using the program Finite Element Method Magnetics,[12] and confirmed with a gaussmeter probe. The 6-well and 24-well plates used for 3D culture were flat bottom ultra low attachment multiple well plates (COSTAR®, 3471 or 3473).

Cells were first cultured in 2D to ~80% confluence, then treated with NANOSHUTTLE™ (NANO3D BIOSCIENCES™, Houston TX) and placed in a standard $CO_2$ cell culture incubator for a 12 hour incubation period. Cells were then trypsinized to detach them from the container and each other. The trypsin was inactivated, and the cells counted and centrifuged and then seeded into individual wells of a 6-well plate using media recommended for their specific cell type. The media volume in each well was 1.0 ml. A magnetic drive was immediately placed above the culture and magnetic forces gently levitate and guide cells together to quickly induce cell-cell interactions and form 3D assemblies. The levitated cultures were then incubated.

For the experiments presented herein, the HEK293 were levitated for 12 hours, and then a hole was punctured in the assembly according to the following procedure. The magnetic drive was removed from above the culture plate and placed below it to gently pull the assembly to the bottom and hold the cells in place. A sterile capillary tube was used to puncture a hole in the cell spheroid. The capillary tubes (DRUMMOND SCIENTIFIC™, Broomall Pa., Cat #1-000-800) had a length of 75 mm, an inner diameter of 0.4 mm, and an outer diameter of 0.8 mm. After removing the capillary tube, a circular defect remained. A capillary tube was found to create a consistent, circular hole, however, to mimic more complex wounds, other-shaped puncture devices could be developed and used.

After creating the wound, the media volume was brought to 1.5 mL and the magnet placed back above the culture to re-levitate the cells. The cell culture plate was placed on a microscope stage to obtain microphotographs by imaging through the central opening in the magnet. The cell culture plate was then placed in the cell culture incubator, but removed for monitoring the cells via microscopy at regular intervals during the wound closure. Cells were maintained by replenishing the media every couple of days.

For another experiment, the human primary fibroblasts (HPF), primary smooth muscle cells (SMC), and a co-culture of these two cells (50% HPF & 50% SMC, or HPF-SMC) were levitated for 4 to 24 hours with the 24-well magnetic levitation system for generating cohesive 3D cultures, and then a hole was generated according to the following procedure.

The magnetic drive was removed from above the culture plate and the cultures were then shredded by means of 4 repeated pippeting action with a P1000 pippette (1,000 microliter). Other mechanical shear or cutting methods can be used for fragmenting the 3D culture, such as vortexing and/or cutting.

An array of 24 ring magnets (¼" outer diameter×¹⁄₁₆" inner diameter×¹⁄₁₆" thick from K&J Magnets, Jamison, Pennsylvania, Model Number: R411) glued on an acrylic plate and distributed to fit under the center of the wells of the 24 well plates were placed underneath the 24 well plate (Ultra Low Attachment Multiple Well Plates, Corning, Inc.) carrying the cultures. The magnetic field from these magnets reshapes (or patterns) the shredded cultures into ring like structures. The inner diameter of these rings is approximately ¹⁄₁₆", however this size can be decreased or increased by increasing or decreasing the number of cells in the well, respectively. Ultra-low attachment plates are usually used, but other plates with other surface modifications can be used as surface for magnetically patterning the shredded cultures, such as cell-adhesive surfaces (often Poly-L-Lysine modified), extracellular matrix coated/modified (including Matrigel™, BD, Inc.), collagen coated, hydrogel modified, and gelatin coated tissue culture plates, and the like.

Once the magnets are placed under the 24 well culture plate and the ring shape is formed, the magnet array is kept static under the culture for a period of 1 to 24 hours inside of the tissue culture incubator. After this incubation period, the 24 well plate is lifted up from the magnet array with a direct vertical motion. Here, no horizontal motion (side-to-side) is desirable in order to not deform the ring shaped structures.

In one embodiment, after patterning the ring shape culture and before removing the magnet array, culture conditions and/or composition can be manipulated, such as: i) by adding cells to the system (these cells can be of the same or different cell type and either carry or not-carry magnetic NANOSHUTTLE™), ii) by adding or overlaying or coating the patterned cells with extracellular matrix, gel, or hydrogel like materials, and/or iii) by adding molecules or nanoparticles that can effect (stimulate or inhibit) the hole closure process of these cultures.

After creating the wound or ring opening, the media volume was kept constant and these structures were allowed to stay at the bottom of the non-adhering tissue culture plate. Thus, the cultures were not re-levitated. The cell culture plate was placed on a microscope stage to obtain microphotographs by imaging through the central opening in the magnet. The cell culture plate was then placed in the cell culture incubator, but removed for monitoring the cells via microscopy at regular intervals during the wound closure. Cells were maintained by replenishing the media every couple of days or as needed.

Single cell and/or combination of cell types (co-culture) not carrying the NANOSHUTTLE™ can be incorporated in these assays (puncturing and magnetic patterning) by layering/pouring them onto the magnetized cells. Cells not carrying the NANOSHUTTLE™ once in contact with the magnetized cells (NANOSHUTTLE™ carrying cells), if compatible with the magnetized cell type, will interact and be incorporated as part of the patterned tissue. Thus, only one cell type needs to be treated or modified with NANOSHUTTLE,™ although more than one cell type can be treated if desired.

Example 2: Cell Viability Assay

Figure 1:
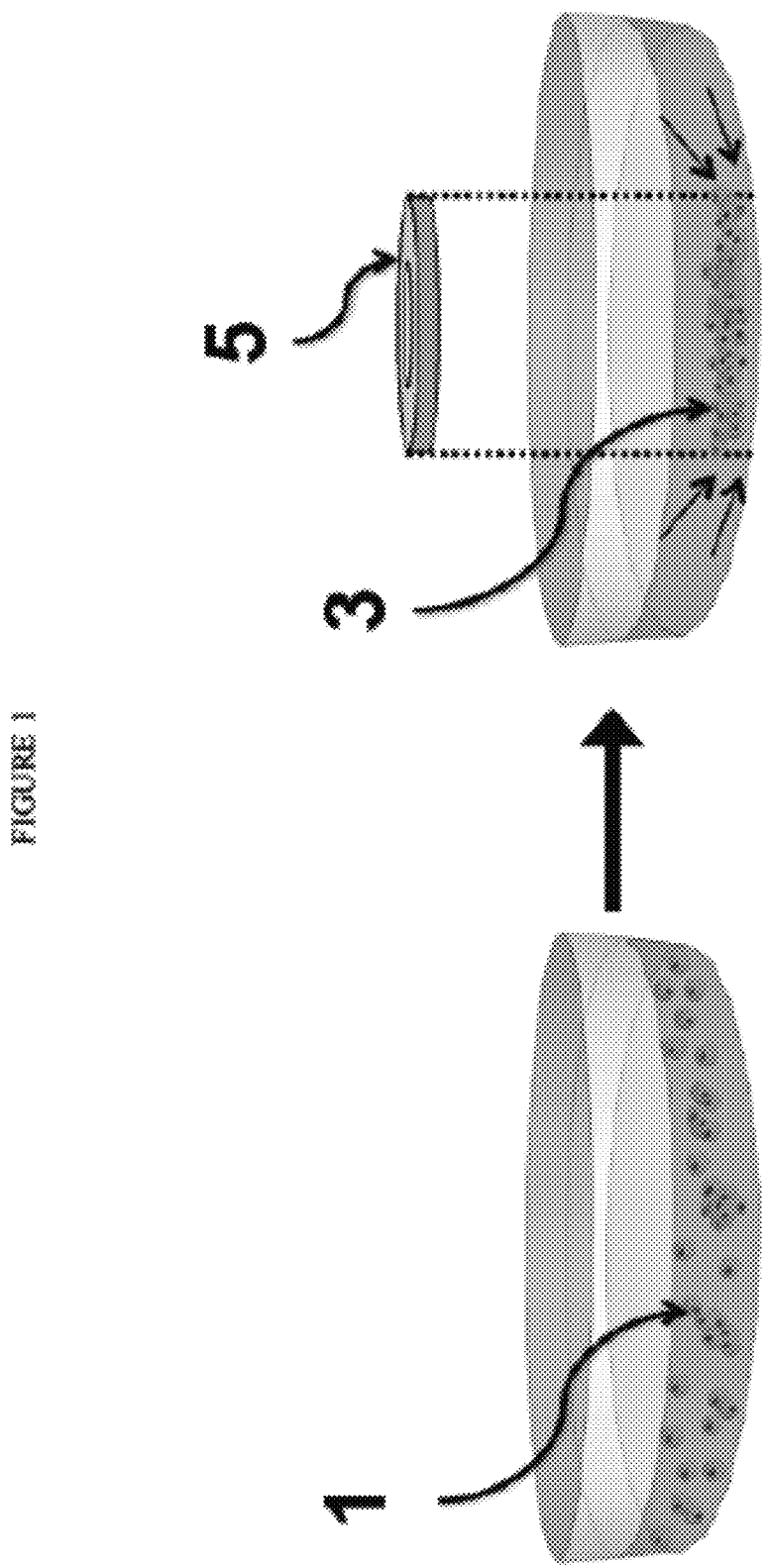
FIG. 1. Schematic of (1) dispersed cells in a petri plate, and magnetically concentrated levitating cells (3) that were gathered using a ring magnet (5).

FIG. 1 shows a schematic of dispersed cells (1) and magnetically concentrated levitating cells (3) grown using a MLM single well device. We have now extended this technique to a commercially available high through-put device including a standard six well culture plate and lid (not shown) together with a specially designed over-lid or secondary cover (6-WELL BIO-ASSEMBLER™ MAGNETIC DRIVE, N3D BIOSCIENCES™) that holds six magnets in place over the six wells. Other array sizes are of course possible. Using the device is as simple as standard 2D techniques, and it has proven to be faster than any other 3D cell culturing product on the market.

The location and shape of the 3D cell assembly can be controlled magnetically by adjusting the position and/or shape of the magnetic field. However, the morphology of the assemblies and amount of time needed to reach a particular stage is cell specific. Some cells types, such as epithelial, form layered sheets and display squamous morphology, while others, such as human umbilical vein endothelial cells, display branching structures. Levitated structures can be separated to create multiple samples and viable cells may be removed from the 3D culture for further experimentation.

No special additional equipment is required and the MLM device is compatible with co-culturing and standard imaging and diagnostic techniques. Cells can be maintained for months and toxins can be introduced into culture and examined for any deleterious effects. Cultures grown with the MLM technology provide a model for natural human tissue, which can be exposed to various drugs and monitored for viability and/or cell-cell interactions.

Figure 2:
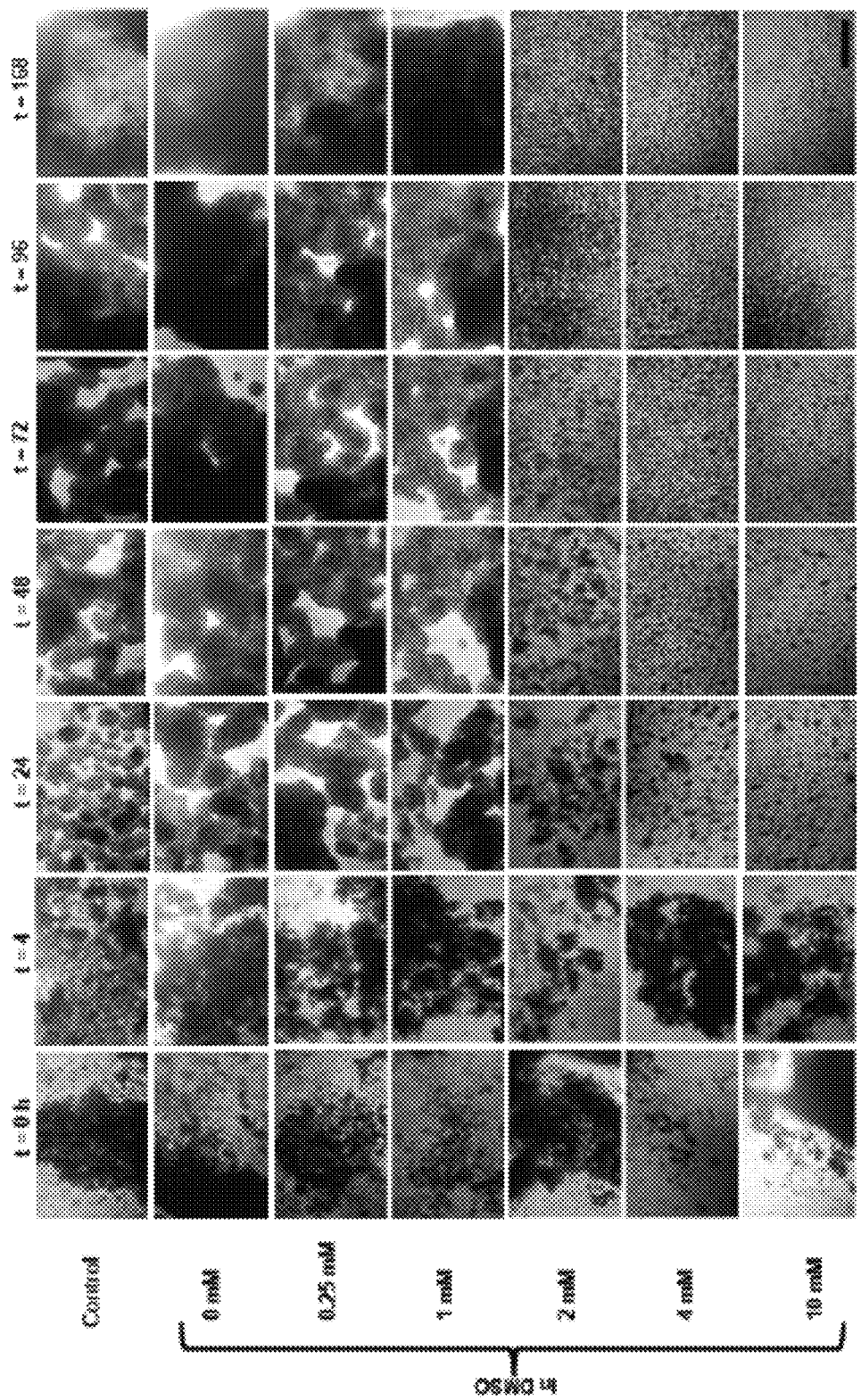
FIG. 2. Phase contrast micrographs of 3D HEK293 morphology at 4× magnification under untreated conditions (control) and after treatment with 0, 0.25, 1, 2, 4, 10 mM of ibuprofen for 0, 4, 24, 48, 72, 96, and 168 hours (scale bar is 500 μm).

FIG. 2 shows exemplary photomicrographs of HEK293 cells cultured in 3D in 6-well plates. Nunc non-treated 6-well cell culture plates were used (6-WELL BIO-ASSEMBLER™ MAGNETIC DRIVE, N3D BIOSCIENCES™), and samples were dosed with varying concentrations of ibuprofen (0 to 10 mM). Cells were pre-levitated for 1 hour before administering the drug and images were obtained at various incubation periods (0 to 168 hours). Images were taken at 4× magnification at the center of the 3D structure.

As ibuprofen dosage concentration or incubation time increased (FIG. 2), the 3D constructs began to appear less cohesive. At high concentrations and incubation times (2 mM, 24 hour), the 3D structures completely disassembled into multiple colonies. This indicates that the ibuprofen is disrupting the cell-cell and cell-matrix interactions and/or cell viability that promote 3D spheroid formation.

When the photomicrographs in FIG. 2 were examined using fractal dimensional analysis (see below for description of how to calculate fractal dimension), overall trends could be observed. Fractal dimension ($D_f$) can be defined as self-similar structures across scales[2] and its analysis has been used in the study of aggregates and cluster formation.[2-3] An increase in the number of individual cell colonies and porosity of a 3D structure with increasing drug concentration and drug incubation time both yield decreases in fractal dimension. This change in fractal dimension can be translated into cell viability or cell-cell interactions. As the fractal dimension of the sample decreases, the percent viability or cell-cell interactions of the cells decreases as well.

Figure 3:
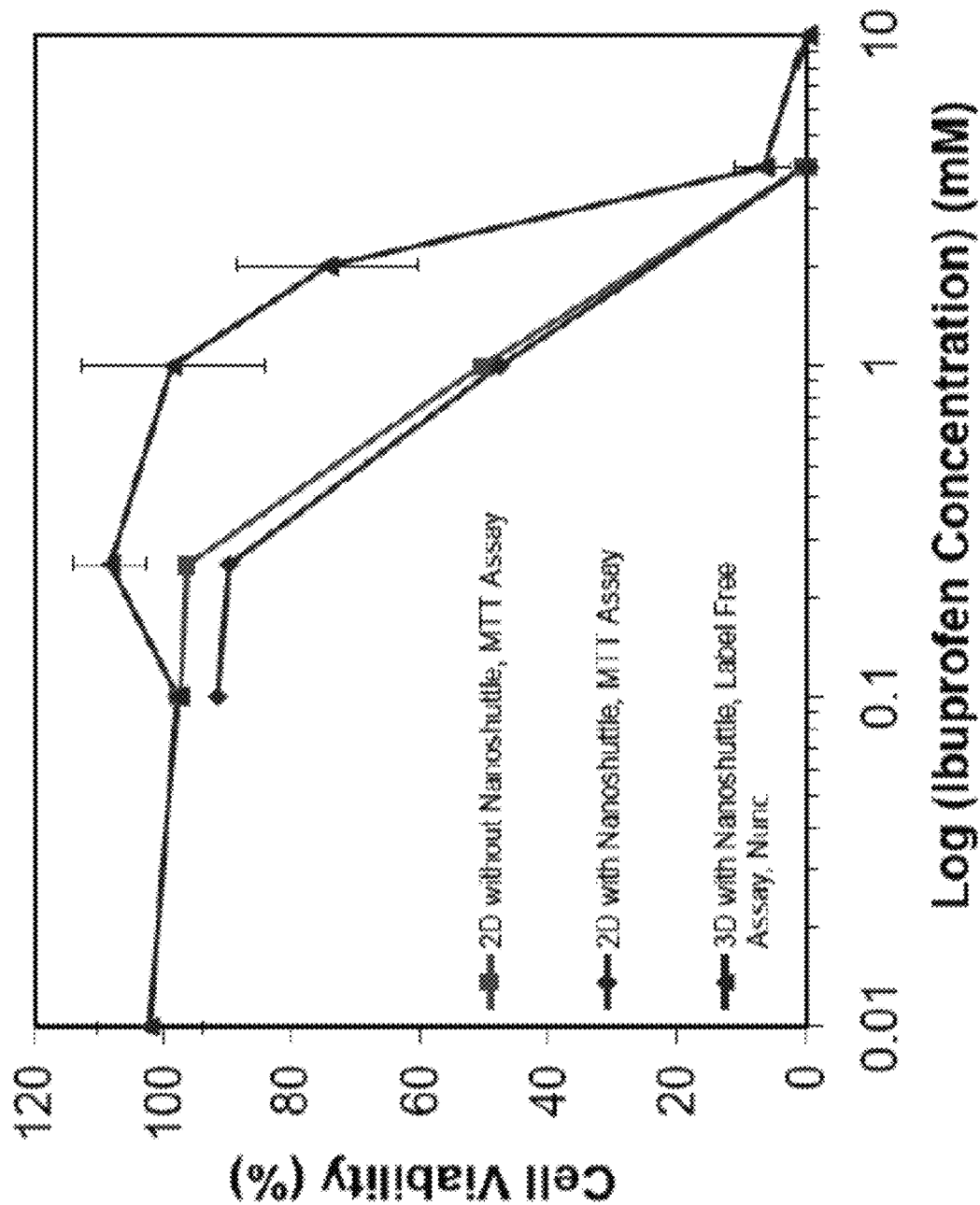
FIG. 3. Percent viability versus the log of ibuprofen concentration for HEK293 cells for a 24 hour dosage time period. For the 3D label-free assay, the data was averaged and error bars are reported. LD50 can be determined by extrapolating the drug concentration at 50% viability.

FIG. 3 shows the percent viability for ibuprofen-dosed HEK293 cells cultured in 2D and assessed with an MTT assay without the presence of NANOSHUTTLE™ (diamonds), with the presence of NANOSHUTTLE™ (squares), and cells cultured in 3D with NANOSHUTTLE™ and assessed with the label-free, fractal analysis assay (triangles). The 24 hour LD50 values (concentration at which half of the cells died after 24 hours) can be extrapolated to approximately 1 mM for cells cultured in 2D and assessed with the MTT assay and 2.2 mM for cells cultured with the MLM and assessed using the label-free assay described above.

The 2D cytotoxicity results presented here compares well with the literature, where a 24 hour LD50 value using an MTT assay was reported to be 1000 µM for ibuprofen in HEK293 cells. We hypothesize that the increase in the LD50 for the 3D assemblies is due to several factors, which include limitations in drug diffusion into the center of the 3D construct and the presence of the ECM and cell-cell interactions, which protect the cells inside the structure from having the same exposure to the drug as those on the outside, so that not all cells are exposed to the drug. These are all aspects that exist within the context of an in vivo tissue, but cannot be easily replicated in 2D monolayer cultures.

Example 3: Image Analysis

The fractal dimension analysis of 2D images can be used to evaluate the structure of fractal-like object agglomerates.[2,4-8] Fractal dimension theory postulates that the relationship between the number of primary objects (N) in a fractal aggregate and its radius of gyration ($R_g$) obeys the following equation:[3-10]

$$N=kg(R_g/a)^{D_f} \qquad \text{Equation 1.}$$

where a is the mean primary object diameter, $D_f$ is the fractal dimension and kg is a constant called the structure prefactor. In this demonstration, we depicted cells as spheres connected to each other. Because fractal-like structures are complex, the determination of $R_g$ is often not trivial.[11] Therefore, we modified the above equation by replacing $R_g$ with the maximum length of the space occupied by the multicellular agglomerate (L):[9,12]

$$N=kg(L/a)^{D_f} \qquad \text{Equation 2.}$$

which can be rewritten as $$D_f=[\log(N)-\log(kg)]/\log(L/a) \qquad \text{Equation 3.}$$

Figure 4:
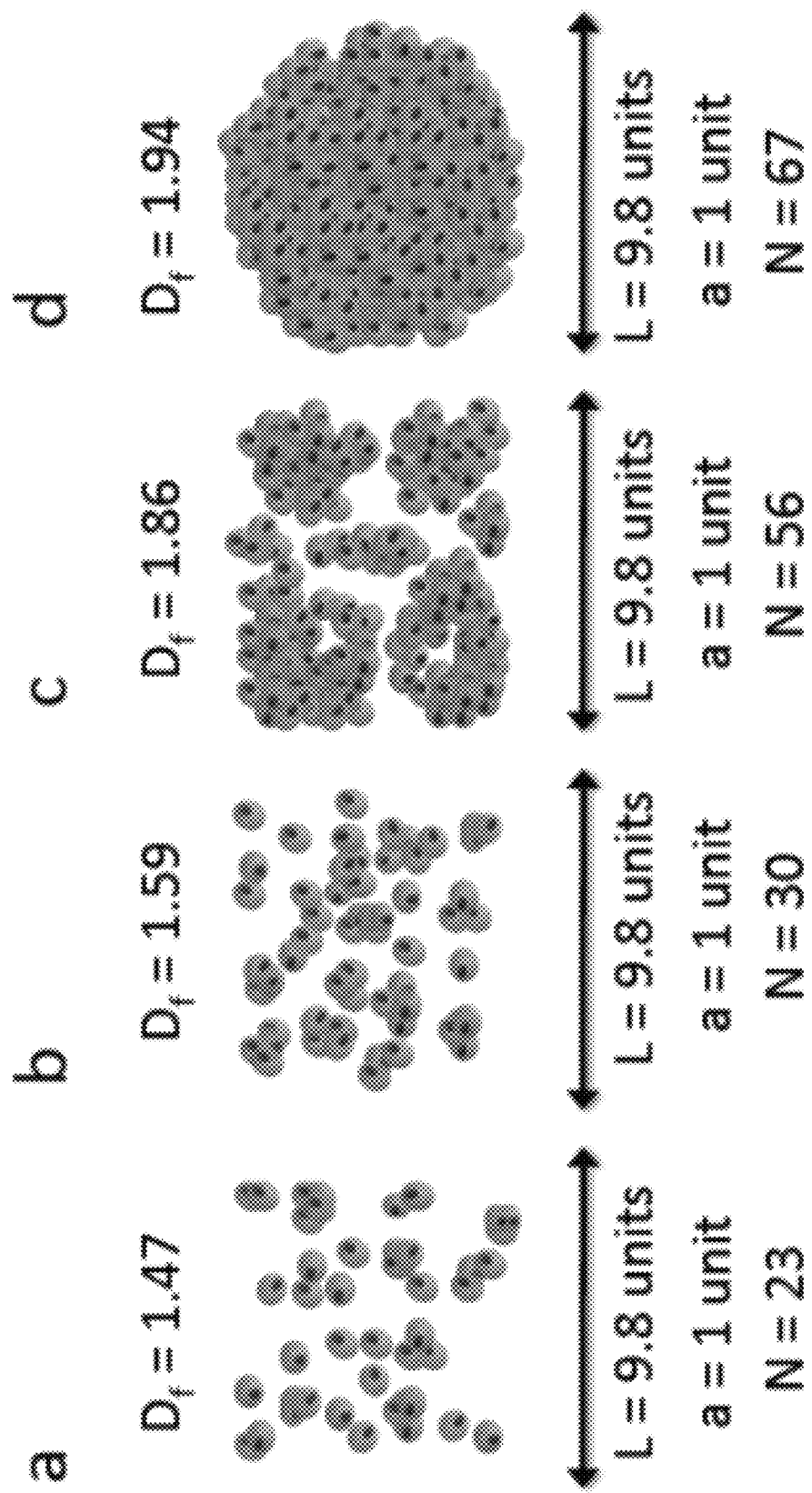
FIG. 4. Simulated fractal theory calculations using the equation.

These equations can be used to evaluate the $D_f$ of modeled systems, as shown in FIG. 4. In this simplified procedure L, a, and kg were kept constant, which makes $D_f$ a function of N, proportional to the log(N). The outcome of this analysis showed that the increase in the number of cells raises the $D_f$ values (FIG. 4, a<b<c<d). These results resonate qualitatively with our $D_f$ analysis and interpretation of 3D multicellular assemblies,[4] where we postulate that the viability of cells (cell replication resulting in increase of N) and cell-cell interaction resulting from viable cells drives the increase in $D_f$ as the drug concentration decreases.

We also calculated the $D_f$ of the structures in FIG. 5 for a simulated change in structure as a function of time using the box-counting method[3,11] (ImageJ software). Generally, box counting consists of a procedure that counts the number of boxes of a given size needed to cover a one pixel wide, binary (black on white) border, where this procedure is repeated for boxes of varying sizes. A curve is plotted where the log of the box count is plotted as a function of the log of the box size. The linearity of this relationship is usually an indication of self-similarity, the main feature of fractal objects. The $D_f$ is evaluated by measuring the slope of the curve generated from plotting the log of the box size versus the log of the number of cells within each box. This method yielded $D_f$ values of 1.89, 1.72, 1.67, and 1.54 representative of multicellular structures (FIG. 5($d$-$g$)).

Although these values follow a similar trend as our experimental results (an increase in $D_f$ as a function of cell density, e.g., FIG. 2 and FIG. 8), the sensitivity of this method to changes in N is inferior to the above calculation. One could increase the dynamic range and sensitivity of the methodology if we could obtain photomicrographs of the various layers of cells, thus taking into account the tissue's three dimensions (3D). The 2D images used herein cannot resolve layers of cells, therefore, only the projection of the multicellular structures is accounted for in the $D_f$ calculation (FIGS. 4, 5). Together, the presented analyses show that the relative measure of $D_f$ allows one to infer the relative number of cells of the multicellular structures as a function of fractal dimension.

Similarly to fractal dimension, cell viability can be also assessed based on the morphological changes in the spheroid structure. Cell viability is calculated using the following equation:

i. Cell viability=,D-fsample.-,D-f100% cell death.-,D-fcontrol.-,D-

$$\text{Cell viability} = \frac{D_{fsample} - D_{f100\% \, cell \, death}}{D_{fcontrol} - D_{f100\% \, cell \, death}}. \quad \text{Equation 4}$$

where $D_{fsample}$ is the fractal dimension of the sample at a particular drug dosage time length t, $D_{fcontrol}$ is the fractal dimension of the negative control at the same dosage time length t, and $D_{f100\%}$ cell death is the fractal dimension of the sample at 100% cell death. This value was obtained from the sample at the highest concentration of drug and longest drug dosage time point. The calculated fractal dimension and percent viability (FIG. 5 ($h,i$)) increases as a function of unimpaired culture time and decreases as a function of toxin concentration.

Next, this method can be used for assays where a foreign agent is replaced by cells of known or unknown type (cells could include heterogeneous mixture of cells types, such as in blood and/or stromal cell fraction). Here, magnetized cells would be used to capture cells from an unknown sample. The cells of this unknown sample could either carry or not the NANOSHUTTLE.™

FIG. 5, parts $j$-$m$, represent a healthy co-culture of two cell types where there is an increasing number of one cell type (small ovals). Here the heterogeneous composition and structure of this culture would be detected by $D_f$ analysis. Part n represents plot of cultures $j$-$m$ with increasing number of cells of one cell type (small ovals) where the other cell type (large ovals) is kept constant. The calculated $D_f$ values are ($j$) 1.418, ($k$) 1.812, ($l$) 1.844, and ($m$) 1.912. $D_f$ versus cell number of one cell type of a co-cultured simulated system ($n$).

Furthermore, if the test cells do not carry any NANOSHUTTLE™ needed for levitation, they would need to be incubated with known cells that carry NANOSHUTTLE™ (these cells would enable levitation and 3D culturing) at the bottom of the non-adhering plate for at least 30 minutes. Alternatively the mixture of cells could be centrifuged to bring them together. Once the multiple cells types are in contact and cell-cell interaction can take place, cells would be levitated together.

In summary, this assay can be used to capture, detect, and characterize homogeneous or heterogeneous cell mixtures, such as isolated stem cells, blood and/or stromal cell mixture.

Based on the simulated data shown above, various plots can be constructed. FIG. 6 shows (a) $D_f$ versus concentration, (b) the number of cells versus concentration, (c) average size versus concentration, (d) total area versus concentration, (e) $D_f$ versus time, (f) number of cells versus time, (g) average size versus time, and (h) total area versus time for the data simulated in FIG. 6.

Based on the three different modalities introduced earlier ($D_f$, size, and size distribution) several analysis methods can be presented. FIG. 7 shows various plots based on the physical data presented in FIG. 2. The (a) fractal dimension, (b) average cluster size (in pixels squared ($px^2$)), and (c) total area ($px^2$) is determined for HEK293 cells exposed to varying concentrations of ibuprofen for 1, 24, and 168 hours. Cell viability based on (d) fractal dimension, (e) average cluster size, and (f) total area is also shown.

When drug dosage decreases (e.g., is washed out), it can be observed that over time, the cells begin to recover and the 3D cultures reassemble. FIG. 8 shows photomicrographs of hepatocytes cultured in 3D with the MLM 6-WELL MAGNETIC DRIVE dosed with varying concentrations of acetaminophen (APAP) (0 to 16 mm). After a change to fresh media without drug, the structures begin to assemble back into a cohesive spheroid.

Example 4: Airborne Toxins

To explore the effects of airborne toxins on magnetically levitating cultures, Bronchial Epithelial Cells (BrEpics) were grown in 3D and exposed to neat xylene vapor. BrEpics were first cultured in 3D for two days in 35 mm×10 mm culture dishes included in the SINGLE WELL BIOASSEMBLER KIT™ (NANO3D BIOSCIENCES™). As the source of xylene vapor, in a sterile cell culture hood, approximately 15 mL of xylene (histological grade, FISHER CHEMICAL™) was placed in a 100 mm×20 mm Pyrex® petri dish and allowed to sit at atmospheric pressure inside a sealed plastic bag. The levitating cells were exposed to the xylene vapors accumulated inside the plastic bag in intervals of 30 minutes. After the repeated exposure to xylene (four times) no cell death was observed. Next, the 35 mm dishes were removed from the large 95 mm×15 mm petri dish holder and placed individually in the bag for 30 minutes increments, followed by 15 minute increments in the $CO_2$ incubator. This was repeated for 1 hour (two times) before cell death was observed. We hypothesize that the large petri dish holder was somehow obstructing the xylene vapors from reaching the cells.

FIG. 9 shows levitating (3D) and non-levitating (bottom, 2D) images of BrEpic cells and cell viability of BrEpics as a function of xylene exposure time using the label-free fractal dimension assay described above. The arrow indicates when cell death was first observed. Levitating pre-xylene treated cells appeared healthy, formed a sheet, and displayed characteristic squamous morphology. Cell death was not observed until the 150 minute xylene exposure time point. Directly before this time point the large petri dish holder was removed so that the xylene vapors could more effectively reach the levitating cells. Increased xylene exposure disrupted the sheet-like formation and non-interacting dead cells remained (FIG. 9, 180 min).

The label-free, fractal analysis assay presented herein for studying cell viability provides a non-invasive way to monitor 3D tissues. With current advances in data processing, this technique may become increasingly important for in vitro toxicity assays. Levitation and growth of the cells can (if desired) occur at the air-liquid interface, which allows for easy introduction of airborne environmental toxins and subsequent monitoring. This particular feature proves useful for studying the lung and exposure to environmental pollutants.

Example 4: Wound Closure

FIG. 1 shows a schematic of magnetically guided tissue sheet formation. Non-levitating dispersed cells (1) are magnetically (5) concentrated (3) in a non-adherent single well culture dish. The flat sheets can be assayed in position or levitated by reversing the magnetic field and used. Additional cells types can also be added thereto, thus building up a complex 3D tissue structure.

A simple physical example of this is demonstrated in FIG. 10, which shows macro- and microphotographs of HEK293 cells cultured after two days in both non-adherent and adherent cell culture dishes. The non-adherent dish shows clear evidence of a 2D tissue sheets formed with the HEK293 cells, while the adherent dish shows isolated cells that have attached to the plastic. A flat sheet of cells, such as those formed in the non-adherent dish, could be used for various applications, like a wound healing assay.

2D scratch cultures were prepared as described in Example 1, photomicrographs were taken at timed intervals and analyzed. Once the images are analyzed, scratch (2D) or hole (3D) closure, referred to as a wound closure for both systems, can be assessed based on morphological changes in structure using the following equation:

$$\text{Wound closure (\%)} = 100\% - \left(\frac{\text{area of wound}_t}{\text{area of wound}_{t0}} \times 100\right) \quad \text{Equation 5}$$

where area of wound$_t$ is the area of the scratch or hole within the field of view in the image of the sample at a particular time t and area of wound$_{t0}$ is the area of the scratch or hole within the field of view in the image of the sample at time zero.

FIG. 11A shows microphotographs of a linear scratch created in 2D monolayer cultures of HEK293 cells grown in the presence of different amounts of fetal bovine serum (FBS). The 0% serum sample showed some cellular debris that dislodged and appeared in the 2, 4, and 24 hour time points; however, it was washed away before the 216 h time point. Also, for the 0% serum at 216 hours, some "rounding" or "balling up" of the cellular clusters near the edge of the scratch was observed. This is not surprising as one of the critiques of the classical linear scratch method is the retraction of cells near the wound edge and the loss of original cell morphology and function due to physical disruption. This "rounding up" 216 h post-scratching may also have been a result of the starvation media conditions due to the absence of serum.

By 216 h, the lines etched in the 10% FBS cultures had completely closed due to cell migration and growth, but the 0% FBS cultures had not. The bright field microscopy images obtained were then analyzed using IMAGEJ software to quantify scratch closure as a function of time and percent serum.

It is important to note that IMAGEJ is a public domain image processing program and that this user-friendly software is available for free through the National Institutes of Health (NIH). No additional costly software or special programming was required to perform this wound-healing assay.

Application of the wound-healing assay to our 3D magnetic levitation system required only a few simple modifications. Rather than seeding the cells (HEK293, HPF, SMC, or HPF-SMC) into adherent wells, the NANOSHUTTLE™-treated cells were seeded in ultra low attachment plates (1.0 mLs of cell/media suspension per well, ~500,000 cells/well in the 6-well; or 320 microLs of cell/media suspension per well, ~500,000 cells/well in the 24-well) and the BIO-ASSEMBLER™ 6-well or 24-well magnetic drive was placed on the lid of each plate.

The levitated cells were first maintained with media with 10% FBS until they coalesced to form a continuous piece of tissue (~4 to 24 hours) in each well. Holes were then made using a glass capillary (with 6-well system and HEK293) or magnetic patterning shredding the 3D structure (with 24-well system and HPF, SMC, and HPF-SMC). In the 6-well each sample and the cells were maintained at a volume of 1.5 mL using media, and in the 24-well each sample and the cells were maintained at a volume of 320 Ls using SMC or HPF media.

As a first test of the wound-healing assay, we studied the response of cells to variation in serum concentration. Increasing the concentration of supplemented serum increases the amount of growth factors and cytokines present, which are necessary for cell division. Therefore, a common result of an increase in the percent of supplemented serum is increased cell proliferation and can thus provide proof of concept for the assay.

FIG. 12 shows photomicrographs of a wound healing assay using HEK293 cells. Two different serum conditions were tested for wound closure generated with the capillary tube approach, and the holes were monitored over time (FIG. 12a). As a function of time, cell migration and new cell growth caused the holes to close up. For this range of hole sizes, when the percent of enclosed area is plotted versus the log of time for the different sized holes at 0 to 5% serum concentration (FIG. 12b), the slopes for these three different sized hole enclosure fits appear very similar (~1). This indicates that the growth rates of the HEK293 cells has little influence for the sized holes and low serum conditions.

We also performed 2D and 3D tests using ibuprofen as a cytotoxic drug. Images were obtained as a function of time and ibuprofen concentration and analyzed as described herein. The control sample consisted of cells without ibuprofen or DMSO, while the 0 mM sample consisted of treating the cells with DMSO (1% in media) without any ibuprofen. By 96 hours, the 0 and 0.1 mM ibuprofen 3D holes had closed (not shown), while the 2D scratch dosed at those same concentrations had still not yet healed after 216 hours (not shown).

For both the 2D and 3D assays performed, it was shown that that time required for healing was reduced at higher serum concentrations. It was also shown that the time required for healing was reduced for 3D as compared to 2D growth conditions. When the test compound ibuprofen was introduced (data not shown), it was shown that the in vitro 3D wound assay could be used as a predictive tool of toxicity. Thus, we have demonstrated that an assay of this nature could be used to distinguish if a test compound is an inhibitor or activator of cell growth and migration or wound closure.

FIG. 13 shows photomicrographs of a wound healing or wound healing assay using HPF, SMC, and co-culture HPF of SMC (HPF-SMC) cells. Two different media conditions were tested, HPF and SMC media, for wound closure generated with the magnetic patterning approach described in Example 1, and the holes were monitored over time. As a function of time, cell migration, 3D culture contraction, and new cell growth caused the holes to close up.

A wound sizes decreased with both media types within the period of 34 hours. The wounds of the cultures in SMC medium (FIG. 13 a-c) did not close over the period of 34 hours. Next, SMC cultures (FIGS. 13 c and f) were not sensitive to media type since these cultures under both media types did not close over the 34 hour period. When comparing wound closure of HPF (FIGS. 13 a and d) cultures and HPF-SMC co-cultures (FIGS. 13 b and e), the wounds of the cultures in fibroblast media (FIGS. 13 d and e) closed under 20 hours in contrast to cultures in SMC media, which did not close over 34 hour period. These results suggest that HPF cells are sensitive to the two different media types and wound closure is accelerated when cells are cultured in HPF media.

A current challenge when co-culturing different cell types is the media condition optimization which is compatible with different cell types to be co-cultured. Thus, we have demonstrated that this assay could be used for optimizing and/or determining media conditions and/or media screening for co-culturing cells based on cell migration, culture contraction, and/or cell proliferation.

The following references are incorporated by reference in their entirety:
1. Chen, C. Y., Pang, V. F. & Chen, C. S. Assessment of ibuprofen-associated nephrotoxicity in renal dysfunction. *J. Pharm. Exp. Ther.* 270, 1307-1312 (1994).
2. Koylu, U. O., Faeth, G. M., Farias, T. L. & Carvalho, M. G. Fractal and projected structure properties of soot aggregates. *Combust. Flame* 100, 621-633 (1995).
3. Dewey, T. G. *Fractals in Molecular Biophysics.* (Oxford University Press, 1997).
4. Souza, G. R. & Miller, J. H. Oligonucleotide detection using angle-dependent light scattering and fractal dimension analysis of gold-DNA aggregates. *J. Am. Chem. Soc.* 123, 6734-6735 (2001).
5. Mandelbrot, B. B. *The Fractal Geometry of Nature.* (Freeman, 1982).
6. Avnir, D., Farin, D. & Pfeifer, P. Molecular fractal surfaces. *Nature* 308, 261-263 (1984).
7. Weitz, D. A., Huang, M., Lin, Y. & Sung, J. Limits of the fractal dimension for irreversible kinetic aggregation of gold colloids. *Phys. Rev. Lett.* 54, 1416-1419 (1985).
8. Brasil, A. M., Farias, T. L. & Carvalho, M. G. Evaluation of the fractal properties of cluster-cluster aggregates. *Aerosol. Sci. Technol.* 33, 440-454 (2000).
9. Souza, G. R. & Miller, J. H. Fractal dimension analysis of gold-biopolymer nanoparticle aggregates using angle dependent light scattering for the detection and characterization of nucleic acids and proteins. Application: US
10. Schroeder, M. *Fractals, Chaos, Power Laws: Minutes from an Infinite Paradise.* (W. H. Freeman and Company, 1992).
11. Smith, T. G. J., D., L. G. & Marks, W. B. Fractal methods and results in cellular morphology. *J. Neurosci. Methods* 69, 1123-1126 (1996).
12. Meeker DC (26 Dec. 2009 Build) Finite Element Method Magnetics, Version 4.2. available at femm.info.

US2003436621
US2004038264
WO2011038370
WO2010036957
61/438,310
US2009137018, WO2005003332
US2005054101, WO2005010162
US2006063252, WO2004083412, WO2004083416

What is claimed is:

1. A label-free method of determining cell viability or cell-cell interaction, comprising:
   a) culturing a sample 3D cell culture comprising a 3D cell culture and a test agent and a control 3D cell culture comprising the 3D cell culture without the test agent, wherein cells of the sample and control 3D cell cultures are levitated in a magnetic field with a composition comprising:
      i) a negatively charged nanoparticle;
      ii) a positively charged nanoparticle; and
      iii) a support molecule,
      wherein one of said negatively charged nanoparticle or positively charged nanoparticle contains a magnetically responsive element, and wherein said support molecule holds said negatively charged nanoparticle and said positively charged nanoparticle in an intimate admixture;
   b) taking photomicrographs of said sample and control 3D cell cultures respectively at one or more times while being levitated in a magnetic field;
   c) analyzing said photomicrographs to measure fractal dimension of the sample and control 3D cell cultures; wherein $D_f=[\log(N)-\log(kg)]/\log(L/a)$ and $D_f$ is a fractal dimension which is a statistical indication of how completely a fractal fills space, wherein said statistical indication is used to approximate a number of cells in a 3D cell culture, kg is a structure prefactor and is a constant, N is a number of cells, a is a diameter of a cell, and L is a length of a box used for box-counting,
   d) determining cell viability based on the measured fractal dimension, wherein $$\text{Cell viability} = \frac{D_{fsample} - D_{f100\% \, cell \, death}}{D_{fcontrol} - D_{f100\% \, cell \, death}},$$

and $D_{fsample}$ is a fractal dimension of the sample 3D cell culture, $D_{fcontrol}$ is a fractal dimension of the control 3D cell culture, and $D_{f100\% \, cell \, death}$ is a fractal dimension of the sample 3D cell culture at 100% cell death and is not zero, wherein fractal dimension is directly proportional to cell viability or cell-cell interactions.

2. The method of claim 1 further including culturing a plurality of sample 3D cell cultures comprising the 3D cell culture and the test agent and culturing a plurality of control 3D cultures comprising the 3D cell culture without the test agent and assessing the effect of said test agent on said cell viability or cell-cell interactions.

3. The method of claim 2, further including adding varying amounts of said test agent to said plurality of sample 3D cultures.

4. The method of claim 3, comprising taking a plurality of photomicrographs of said sample and control 3D cell cultures, respectively, at a plurality of times.

5. The method of claim 3, further comprising washing out said test agent from said plurality of sample 3D cultures and taking a further plurality of photomicrographs of said washed sample 3D cell cultures at a further plurality of times.

6. The method of claim 1, a) wherein the support molecule is selected from the group consisting of peptides, polysaccharides, nucleic acids, polymers, poly-lysine, fibronectin, collagen, laminin, BSA, hyaluronan, glycosaminoglycan, anionic, non-sulfated glycosaminoglycan, gelatin, extracellular matrix protein mixtures, antibody, and mixtures thereof, b) wherein said negatively charged nanoparticle is a gold nanoparticle, and c) wherein said positively charged nanoparticle is an iron oxide nanoparticle.

7. The method of claim 1, wherein the composition comprises a nanoparticle assembly of a gold nanoparticle, an iron oxide nanoparticle and a poly-l-lysine support molecule.

8. The method of claim 3, wherein a decrease in cell viability with said test agent indicates that the test agent is inhibitory, and wherein an increase in cell viability indicates that said test agent is stimulatory.

9. The method of claim 1, further comprising:
analyzing said photomicrographs in step c) to measure one or more of i) a number of sample or control 3D cell cultures, ii) a size of sample or control 3D cell cultures, and iii) a total area of sample or control 3D cell cultures;
wherein fractal dimension and 3D cell culture size are directly proportional to cell viability or cell-cell interactions, and
wherein the number of 3D cell cultures and total area of 3D cell cultures are inversely proportional to cell viability or cell-cell interactions.

10. A label-free method of determining cell viability or cell-cell interaction in the presence of a test agent, comprising:
a) culturing a plurality of magnetic cells levitated in a magnetic field to form a plurality of 3D cell cultures, one or more of said plurality of the 3D cell cultures being without a test agent representing one or more control 3D cell cultures, and one or more of said plurality of the 3D cell cultures being with one or more concentrations of said test agent representing one or more sample 3D cell cultures;
b) taking photomicrographs of said one or more control 3D cell cultures or sample 3D cell cultures levitated in a magnetic field at one or more times;
c) analyzing said photomicrographs to measure fractal dimension of said one or more control 3D cell cultures or sample 3D cell cultures;
wherein $D_f=[\log(N)-\log(kg)]/\log(L/a)$ and $D_f$ is a fractal dimension, which is a statistical indication of how completely a fractal fills space, wherein said statistical indication is used to approximate a number of cells in a 3D cell culture, kg is a structure prefactor and is a constant, N is a number of cells, a is a diameter of a cell, and L is a length of a box used for box-counting,
d) determining cell viability based on the measured fractal dimension, wherein $$\text{Cell viability} = \frac{D_{fsample} - D_{f100\% \ cell \ death}}{D_{fcontrol} - D_{f100\% \ cell \ death}},$$

and $D_{fsample}$ is a fractal dimension of the sample 3D cell culture, $D_{fcontrol}$ is a fractal dimension of the control 3D cell culture, and $D_{f100\% \ cell \ death}$ is a fractal dimension of the sample 3D cell culture at 100% cell death and is not zero,
wherein fractal dimension is directly proportional to cell viability or cell-cell interactions.

11. The method of claim 10, wherein said method is used to assess the effects of said test agent on toxicity, mitotic activity, growth stimulation, cell-cell interactions, cell-matrix interactions, viability, cell structure, or to optimize culture media.

12. The method of claim 10, further comprising:
analyzing said photomicrographs in step c) to measure one or more of i) a number of sample or control 3D cell cultures, ii) a size of sample or control 3D cell cultures, and iii) a total area of sample or control 3D cell cultures;
wherein fractal dimension and 3D cell culture size are directly proportional to cell viability or cell-cell interactions, and
wherein the number of 3D cell cultures and total area of 3D cell cultures are inversely proportional to cell viability or cell-cell interactions.

13. A label-free method for determining cell-cell interaction or viability in the presence of a test agent, comprising:
a) culturing a plurality of 3D cell cultures, one or more of said plurality of 3D cell cultures being without a test agent representing one or more control 3D cell cultures, and one or more of said plurality of 3D cell cultures being with one or more concentrations of said test agent representing one or more sample 3D cell cultures;
b) taking photomicrographs of said plurality of said one or more control 3D cell cultures or sample 3D cell cultures at one or more times;
c) analyzing said photomicrographs to measure fractal dimension of said one or more control 3D cells cultures or sample 3D cell cultures,
wherein $D_f=[\log(N)-\log(kg)]/\log(L/a)$ and $D_f$ is a fractal dimension, which is a statistical indication of how completely a fractal fills space, wherein said statistical indication is used to approximate a number of cells in a 3D cell culture, kg is a structure prefactor and is a constant, N is a number of cells, a is a diameter of a cell, and L is a length of a box used for box-counting,
d) determining cell viability based on the measured fractal dimension, wherein $$\text{Cell viability} = \frac{D_{fsample} - D_{f100\% \ cell \ death}}{D_{fcontrol} - D_{f100\% \ cell \ death}},$$

and $D_{fsample}$ is a fractal dimension of the sample 3D cell culture, $D_{fcontrol}$ is a fractal dimension of the control 3D cell culture, and $D_{f100\% \ cell \ death}$ is a fractal dimension of the sample 3D cell culture at 100% cell death and is not zero,
wherein fractal dimension is directly proportional to cell-cell interaction and viability,
and wherein a decrease in cell-cell interaction indicates that said test agent is inhibitory, and wherein an increase in cell-cell interactions indicates that said test agent is stimulatory;
e) wherein said plurality of 3D cell cultures are prepared by levitating cells in a magnetic field with a composition comprising: a) a negatively charged nanoparticle; b) a positively charged nanoparticle; and c) a support molecule, wherein said negatively charged nanoparticle or positively charged nanoparticle contains a magnetically responsive iron or iron oxide, and wherein said support molecule holds said negatively charged nanoparticle and said positively charged nanoparticle in an intimate admixture.

14. The method of claim 13, a) wherein the support molecule is selected from the group consisting of peptides, polysaccharides, nucleic acids, polymers, poly-lysine, fibronectin, collagen, laminin, BSA, hyaluronan, glycosaminoglycan, anionic, non-sulfated glycosaminoglycan, gelatin, extracellular matrix protein mixtures, antibody, and mixtures thereof, b) wherein said negatively charged nanoparticle is a gold nanoparticle, and c) wherein said positively charged nanoparticle is an iron oxide nanoparticle.

15. The method of claim 13, wherein the composition comprises a nanoparticle assembly of a gold nanoparticle, an iron oxide nanoparticle and a poly-l-lysine support molecule.

16. The method of claim 13, wherein the test agent is a drug, a cell type, a cell component, a toxin or an environmental agent.

17. The method of claim 13, wherein the test agent is a layer or coat of extracellular matrix, gel, or hydrogel.

18. The method of claim 13, further comprising:
analyzing said photomicrographs in step c) to measure one or more of i) a number of sample or control 3D cell cultures, ii) a size of sample or control 3D cell cultures, and iii) a total area of sample or control 3D cell cultures;
wherein fractal dimension and 3D cell culture size are directly proportional to cell viability or cell-cell interactions, and
wherein the number of 3D cell cultures and total area of 3D cell cultures are inversely proportional to cell viability or cell-cell interactions.

* * * * *